US011986486B2

(12) United States Patent
Yu

(10) Patent No.: US 11,986,486 B2
(45) Date of Patent: May 21, 2024

(54) AQUEOUS COMPOSITIONS OF BORTEZOMIB

(71) Applicant: Spes Pharmaceuticals Inc., North Brunswick, NJ (US)

(72) Inventor: Jianwei Yu, Plainsboro, NJ (US)

(73) Assignee: SPES PHARMACEUTICALS INC., North Brunswick, NJ (US)

( * ) Notice: Subject to any disclaimer, the term of this patent is extended or adjusted under 35 U.S.C. 154(b) by 0 days.

(21) Appl. No.: 17/516,400

(22) Filed: Nov. 1, 2021

(65) Prior Publication Data
US 2022/0133757 A1 May 5, 2022

Related U.S. Application Data

(60) Provisional application No. 63/125,563, filed on Dec. 15, 2020, provisional application No. 63/108,509, filed on Nov. 2, 2020.

(51) Int. Cl.
| | | |
|---|---|---|
| A61K 31/69 | (2006.01) | |
| A61K 9/08 | (2006.01) | |
| A61K 47/18 | (2017.01) | |
| A61K 47/20 | (2006.01) | |
| A61K 47/26 | (2006.01) | |

(52) U.S. Cl.
CPC ............. *A61K 31/69* (2013.01); *A61K 9/08* (2013.01); *A61K 47/183* (2013.01); *A61K 47/20* (2013.01); *A61K 47/26* (2013.01)

(58) Field of Classification Search
CPC ........ A61K 31/69; A61K 9/08; A61K 47/183; A61K 47/20; A61K 47/26
See application file for complete search history.

(56) References Cited

U.S. PATENT DOCUMENTS

| | | | |
|---|---|---|---|
| 8,962,572 B2 | 2/2015 | Usayapant et al. | |
| 9,095,514 B2 | 8/2015 | Namdeo et al. | |
| 9,180,093 B2 | 11/2015 | Soppimath et al. | |
| 10,314,880 B2 | 6/2019 | Kanteepan et al. | |
| 2011/0178470 A1 | 7/2011 | Kocherlakota et al. | |
| 2011/0230441 A1 | 9/2011 | Soppimath et al. | |
| 2012/0083457 A1 | 4/2012 | Usayapant et al. | |
| 2014/0276482 A1* | 9/2014 | Astafieva ............... | A61K 47/14 604/294 |
| 2017/0143622 A1 | 5/2017 | Shaik et al. | |
| 2017/0224730 A1* | 8/2017 | Berenson ............... | A61K 33/36 |
| 2018/0110822 A1* | 4/2018 | Chandrashekhar .. | A61K 9/0019 |

FOREIGN PATENT DOCUMENTS

| | | | | |
|---|---|---|---|---|
| WO | WO 2002/059130 | * | 8/2002 | .......... C07K 5/0827 |
| WO | 2016059590 A1 | | 4/2016 | |
| WO | 2017013208 A1 | | 1/2017 | |
| WO | 2017013209 A1 | | 1/2017 | |
| WO | 2018164513 A1 | | 9/2018 | |
| WO | 2019097413 A1 | | 5/2019 | |
| WO | 2020144607 A1 | | 7/2020 | |

OTHER PUBLICATIONS

Committee for Human MEdicinal PRoducts, Benzyl Alcohol and benzoic acid group used as excipients, Oct. 9, 2017, 1-16 (Year: 2017).*
Notification of Transmittal of the International Search Report and the Written Opinion for corresponding International Application No. PCT/US21/57556, mailed Feb. 1, 2022, 16 pages.

* cited by examiner

*Primary Examiner* — Susanna Moore
*Assistant Examiner* — Luisalberto Gonzalez
(74) *Attorney, Agent, or Firm* — Nixon & Vanderhye P.C.

(57) ABSTRACT

Provided herein are novel ready-to-use bortezomib formulations, methods of preparing, and methods of using the same.

16 Claims, 1 Drawing Sheet

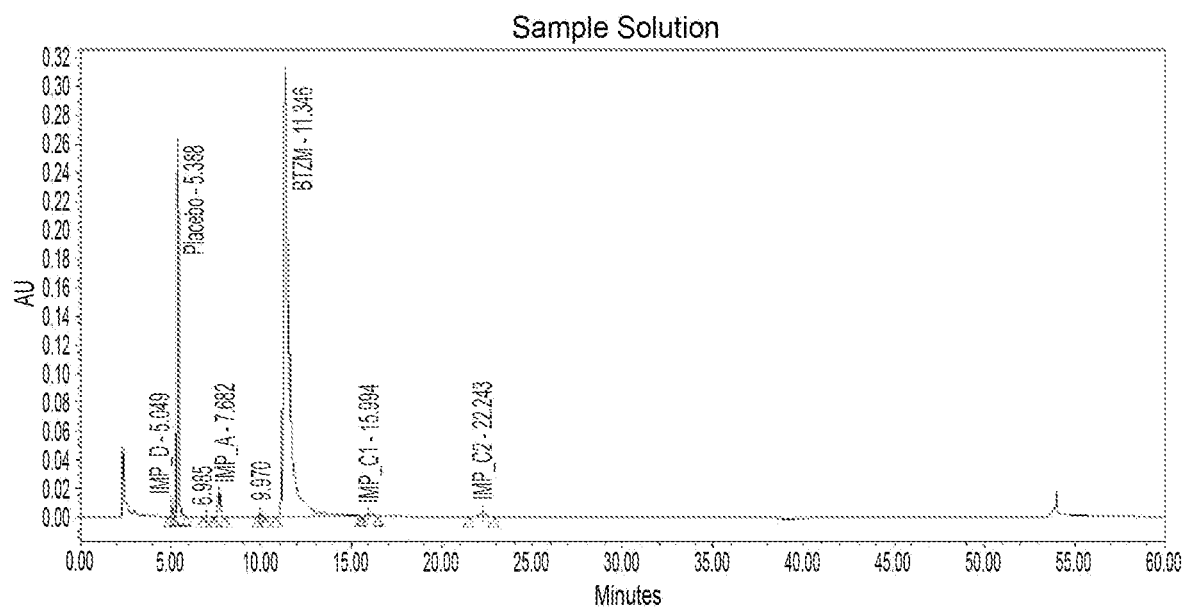
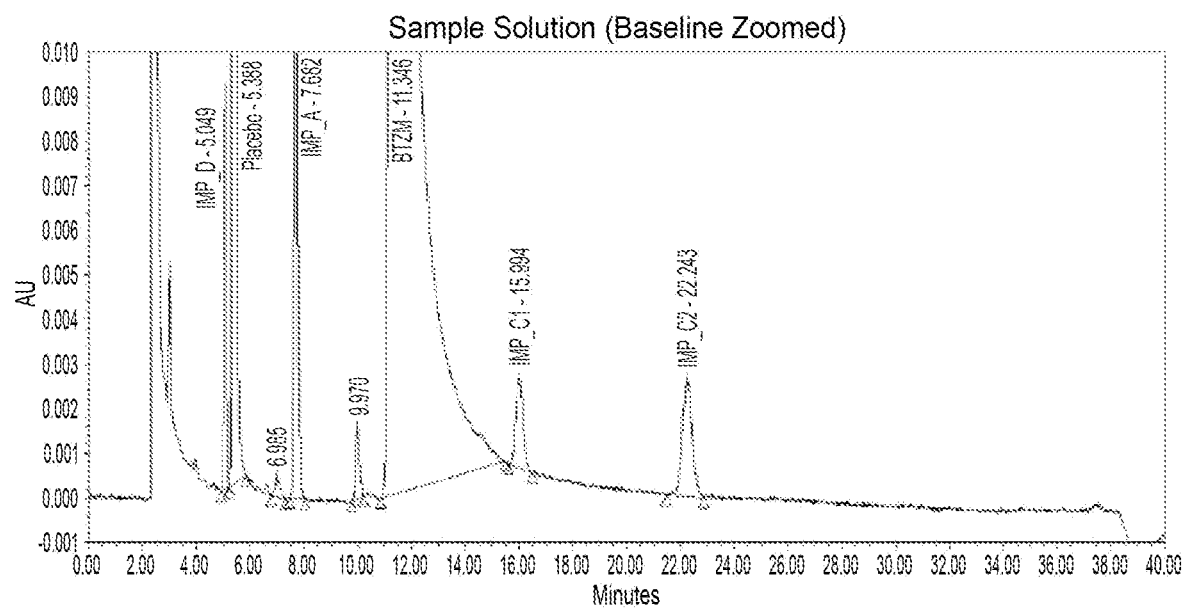

AQUEOUS COMPOSITIONS OF BORTEZOMIB

CROSS REFERENCE TO RELATED APPLICATIONS

This application claims the benefit of U.S. Provisional Application Nos. 63/108,509, filed Nov. 2, 2020, and 63/125,563, filed Dec. 15, 2020, the content of each of which is incorporated herein by reference in its entirety.

This disclosure generally relates to the field of liquid compositions of bortezomib, methods of preparation, and methods of using the same, for example, in treating or preventing cancer.

BACKGROUND

Bortezomib is a modified dipeptidyl boronic acid. The chemical name for bortezomib, the monomeric boronic acid, is [(1R)-3-methyl-1-[[(2S)-1-oxo-3-phenyl-2-[(pyrazinylcarbonyl) amino]propyl]amino]butyl]boronic acid.

Bortezomib has the following chemical structure:

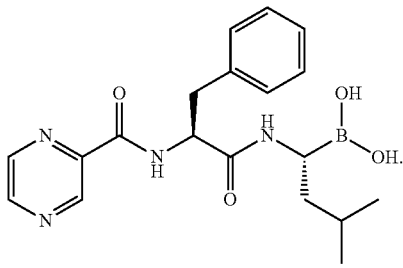 [SMILES: CC(C)C[C@H](NC(=O)[C@H](Cc1ccccc1)NC(=O)c1cnccn1)B(O)O]

The boron atom in bortezomib tends to bind the catalytic site of the 26S proteasome with high affinity and specificity. In normal cells, the proteasome regulates protein expression and function by degradation of ubiquitylated proteins, and also rids the cell of abnormal or misfolded proteins. Clinical and preclinical data support a role for the proteasome in maintaining the immortal phenotype of myeloma cells, and cell-culture and xenograft data support a similar function in solid tumor cancers. Not to limit other mechanisms likely involved, proteasome inhibition may prevent degradation of pro-apoptotic factors, thereby triggering programmed cell death in neoplastic cells.

Bortezomib is cytotoxic to a variety of cancer types in vitro and suppresses tumor cell growth, induces apoptosis, overcomes resistance to standard chemotherapy agents and radiation therapy, and inhibits angiogenesis. Bortezomib is an approved antineoplastic agent, it is indicated for the treatment of adult patients with multiple myeloma and for the treatment of adult patients with mantle cell lymphoma.

Bortezomib was known to be unstable, especially in a liquid state, such as in an aqueous solution. All three currently marketed products of bortezomib are provided in a solid form such as a lyophilized powder, which require reconstitution prior to use. The reconstituted solution is typically only "stable" for up to 8 hours.

BRIEF SUMMARY

In various embodiments, the present disclosure generally relates to liquid formulations, such as aqueous compositions, containing bortezomib, which are typically storage stable for an extended period of time. In some embodiments, the liquid formulations can be a ready-to-use formulation, which can be directly used for administration to a subject in need, e.g., a cancer patient in need, without further handling and manipulation, such as reconstitution and dilution. In some embodiments, the liquid formulations can also be a ready-to-dilute formulation, which can be diluted and then used for administration to a subject in need.

The present disclosure is based in part on the unexpected discovery that certain combinations of excipients, such as antioxidant and different polyhydroxy excipients, effectively slowed down the degradation of bortezomib in aqueous solutions. With the enhanced stability, the bortezomib formulations herein can be formulated as ready-to-use formulations, which can be advantageous in various aspects. For example, without the need to handle and manipulate the cytotoxic bortezomib in a solid state, administering bortezomib to patients can be greatly simplified, which also reduces the risk of errors in the reconstitution step. In addition, as the manufacturing processes of the bortezomib formulations herein typically do not require a lyophilization step, it is expected that the production cost for the bortezomib formulations herein would be significantly lower than that of the currently marketed products. Further, the bortezomib formulations herein can be formulated as a single-dose or multiple-dose dosage forms, which can minimize drug waste and can simplify packaging and storing of the medicine.

The bortezomib formulations herein are typically in an aqueous form, for example, in the form of an aqueous solution, which can contain water in an amount of greater than 50% by weight, e.g., about 60%, about 70%, about 80%, about 85%, about 90%, about 95%, or any ranges between the recited values, such as about 60-85%, about 60-95%, about 70-80%, about 70-90%, etc. In some embodiments, the bortezomib formulations can be a ready-to-use aqueous composition, such as a ready-to-use aqueous solution, which can be administered to a subject in need directly. In some embodiments, the bortezomib formulations can be a ready-to-dilute aqueous composition, such as a ready-to-dilute aqueous solution, which can be administered to a subject in need after dilution to a desired concentration.

In some embodiments, the bortezomib formulations herein can also be in a solid form. The solid form typically can be prepared by removing the liquid components of a liquid bortezomib formulation herein through common pharmaceutical processes, such as lyophilization. Reconstituting such solid form can provide a reconstituted solution, which can be used, for example, in cancer therapy. Unlike the reconstituted aqueous solutions prepared from the currently marketed products, which are only stable for up to about 8 hours, the reconstituted aqueous solutions from the solid forms of bortezomib formulations herein can also be storage stable for an extended period of time, such as for a month, 3 months, or longer.

The bortezomib formulations herein are typically storage stable. For example, in some embodiments, the bortezomib formulations herein, when stored at room temperature or at 40° C. for 1 month or longer, such as for 3 months or longer, can have the bortezomib content maintained at or above 90% (e.g., about 90%, about 95%, about 98%, or higher) of the initial bortezomib amount with a level of total impurities of 10% or less (such as less than 10%, less than 8%, less than 6%, less than 4%, less than 2%, or less than 1%). The level of impurities as described herein should be understood as based on HPLC area %, unless otherwise specified. Suitable HPLC methods are described herein in the Examples section herein.

In some embodiments, the present disclosure provides aqueous compositions of bortezomib, which comprises bortezomib or its pharmaceutically acceptable form and at least one polyhydric or polyhydroxy pharmaceutical excipient, such as sugar alcohol or polyhydric alcohol containing multiple hydroxyl groups (—OH), and/or a water-soluble derivative of cyclic oligosaccharides, such as a water-soluble derivative of β-cyclodextrin, and an antioxidant, such as a sulfur containing antioxidant, such as a sulfur containing amino acid in a liquid vehicle, such as an aqueous vehicle. In some embodiments, the aqueous vehicle is essentially free of an organic solvent. Typically, the liquid compositions of bortezomib exhibits extended physical and chemical stability.

Typically, the aqueous composition comprises bortezomib in an amount from about 0.5 mg/mL to about 3.5 mg/mL and at least one polyhydric or polyhydroxy pharmaceutical excipient. In some embodiments, the aqueous composition comprises a combination of at least one polyhydric alcohol and one water-soluble derivative of cyclic oligosaccharide. In some embodiments, the at least one polyhydric alcohol and one water-soluble derivative of cyclic oligosaccharide exhibit at least an additive effect, such as a synergistic effect, on bortezomib stabilization in aqueous media. In some embodiments, the aqueous composition is essentially free of an organic solvent. In some embodiments, the aqueous composition can also include an antioxidant.

In some embodiments, the present disclosure provides a stable aqueous composition of bortezomib. In some embodiments, the stable aqueous composition comprises about 0.5 mg/mL to about 3.5 mg/mL of bortezomib and at least one polyhydric alcohol and/or one derivative of β-cyclodextrin. In some embodiments, the weight ratio of bortezomib to the at least one polyhydric alcohol is in between about 1:10 to about 1:200, preferably from about 1:20 to about 1:150 of weight ratio. In some embodiments, the stable aqueous composition comprises at least one antioxidant.

In some embodiments, the present disclosure provides a ready-to-use aqueous compositions of bortezomib. In some embodiments, the ready-to-use aqueous composition has a preferred pH range of 0.5 to 5.0, which comprises about 0.5 mg/mL to about 3.5 mg/mL of bortezomib or a pharmaceutically acceptable salt form, at least one polyhydric alcohol, or a combination of at least one polyhydric alcohol and at least one water-soluble derivative of cyclic oligosaccharide, e.g., a derivative of β-cyclodextrin, wherein the weight ratio of the polyhydric alcohol and the water-soluble derivative of cyclic oligosaccharide is between about 1:5 to about 5:1. In some embodiments, the ready-to-use aqueous composition comprises one or more antioxidants, particularly preferred those antioxidants suitable for parenteral administration, such as phenolic antioxidants, sulfur containing water-soluble antioxidants, etc. Typically, the ready-to-use bortezomib compositions herein exhibit exceptionally physical and chemical stabilities on storage for an extended period of time at 25° C. or 40° C.

Optionally the bortezomib compositions, such as the aqueous compositions of bortezomib herein may comprise other suitable additives, such as antimicrobial preservative, chelating agent, and buffer agent, inert gas, etc.

In some embodiments, the present disclosure provides the following exemplary embodiments [1]-[119]:
 [1] A pharmaceutical composition comprising (1) bortezomib; (2) a polyhydric alcohol; and (3) a water-soluble antioxidant (e.g., a phenolic or sulfur containing antioxidant suitable for parenteral administration), wherein the pharmaceutical composition is in a liquid form.
 [2] The pharmaceutical composition of [1], which is a ready-to-use aqueous solution, wherein the aqueous solution comprises water in an amount of greater than 50% by weight, e.g., about 60%, about 70%, about 80%, about 85%, about 90%, about 95%, or any ranges between the recited values, such as about 60-85%, about 60-95%, about 70-80%, about 70-90%, etc.
 [3] The pharmaceutical composition of [1] or [2], wherein the bortezomib is present in the pharmaceutical composition in a concentration ranging from about 0.5 mg/mL to about 3.5 mg/mL, e.g., about 1 mg/mL, about 1.5 mg/mL, about 2 mg/mL, about 2.5 mg/mL, about 3 mg/mL or about 3.5 mg/mL, or any ranges between the recited values.
 [4] The pharmaceutical composition of any one of [1]-[3], wherein the polyhydric alcohol comprises mannitol.
 [5] The pharmaceutical composition of any one of [1]-[4], wherein the weight ratio of bortezomib to the polyhydric alcohol ranges from about 1:10 to about 1:200, e.g., about 1:20, about 1:50, about 1:100, about 1:150, or about 1:200, or any ranges between the recited values.
 [6] The pharmaceutical composition of any one of [1]-[5], wherein the pharmaceutical composition comprises a water-soluble cyclodextrin.
 [7] The pharmaceutical composition of [6], wherein the weight ratio of the polyhydric alcohol to the water-soluble cyclodextrin ranges from about 1:5 to about 5:1, e.g., about 1:3, about 1:1, about 2:1, about 5:1, or any ranges between the recited values.
 [8] The pharmaceutical composition of [6] or [7], wherein the water-soluble cyclodextrin comprises hydroxypropyl β-cyclodextrin (HPβCD), sulfobutyl ether β-cyclodextrin (SBEβCD), or a combination thereof.
 [9] The pharmaceutical composition of any one of [1]-[5], wherein the pharmaceutical composition comprises (1) bortezomib; (2) mannitol; (3) a water-soluble cyclodextrin; and (4) the water-soluble antioxidant.
 [10] The pharmaceutical composition of [9], wherein the weight ratio of the mannitol to the water-soluble cyclodextrin ranges from about 1:5 to about 5:1, e.g., about 1:3, about 1:1, about 2:1, about 5:1, or any ranges between the recited values.
 [11] The pharmaceutical composition of [9] or [10], wherein the water-soluble cyclodextrin comprises hydroxypropyl β-cyclodextrin (HPβCD), sulfobutyl ether β-cyclodextrin (SBEβCD), or a combination thereof.
 [12] The pharmaceutical composition of any one of [1]-[11], wherein the pharmaceutical composition further comprises propylene glycol, benzyl alcohol, or a combination thereof.
 [13] The pharmaceutical composition of [12], wherein the propylene glycol, benzyl alcohol, or combination thereof is present in a concentration of about 5 mg/mL to about 100 mg/mL, such as about 10 mg/mL to about 100 mg/mL, e.g., about 5 mg/mL, about 10 mg/mL, about 50 mg/mL, about 100 mg/mL, or any ranges between the recited values such as about 10-50 mg/mL or about 5-50 mg/mL.
 [14] The pharmaceutical composition of any one of [1]-[5], wherein pharmaceutical composition comprises (1)

bortezomib; (2) mannitol; (3) propylene glycol, benzyl alcohol, or a combination thereof; and (4) the water-soluble antioxidant.

[15] The pharmaceutical composition of [14], wherein the propylene glycol, benzyl alcohol, or combination thereof is present in a concentration of about 5 mg/mL to about 100 mg/mL, such as about 10 mg/mL to about 100 mg/mL, e.g., about 5 mg/mL, about 10 mg/mL, about 50 mg/mL, about 100 mg/mL, or any ranges between the recited values such as about 10-50 mg/mL or about 5-50 mg/mL.

[16] The pharmaceutical composition of any one of [1]-[15], wherein the water-soluble antioxidant is present in a concentration of about 0.1 mg/mL to about 10 mg/mL, such as about 0.5 mg/mL to about 10 mg/mL, e.g., about 0.5 mg/mL, about 1 mg/mL, about 2 mg/mL, about 5 mg/mL, about 10 mg/mL, or any ranges between the recited values.

[17] The pharmaceutical composition of any one of [1]-[16], wherein the water-soluble antioxidant comprises a sulfur containing amino acid, such as methionine, or the water-soluble antioxidant comprises monothioglycerol, sodium metabisulfite, butylated hydroxyanisole and/or butylated hydroxytoluene.

[18] The pharmaceutical composition of any one of [1]-[17], comprising a preservative, a chelating agent, an osmotic agent, a buffer, or a combination thereof.

[19] The pharmaceutical composition of any one of [1]-[18], which has an aqueous pH of about 1.5 to about 5.0, such as about 1.5, about 2, about 3, about 3.5, about 4, about 4.5, about 5, or any ranges between the recited values.

[20] The pharmaceutical composition of any one of [1]-[19], which is essentially free of dissolved oxygen.

[21] The pharmaceutical composition of any one of [1]-[20], which is storage stable.

[22] The pharmaceutical composition of any one of [1]-[21], which is in a single-dose dosage form, e.g., packaged in an ampoule, a vial, a cartridge, a pre-filled syringe, an intravenous bag.

[23] The pharmaceutical composition of any one of [1]-[21], which is in a multi-dose dosage form.

[24] An aqueous solution suitable for pharmaceutical use (e.g., parenteral injection, such as intravenous or subcutaneous injection), the aqueous solution comprising bortezomib, mannitol, and sulfobutyl ether beta-cyclodextrin, wherein the aqueous solution comprises water in an amount of greater than 50% by weight, e.g., about 60%, about 70%, about 80%, about 85%, about 90%, about 95%, or any ranges between the recited values, such as about 60-85%, about 60-95%, about 70-80%, about 70-90%, etc.

[25] The aqueous solution of [24], wherein the bortezomib is present in a concentration ranging from about 0.5 mg/mL to about 3.5 mg/mL, e.g., about 1 mg/mL, about 1.5 mg/mL, about 2 mg/mL, about 2.5 mg/mL, about 3 mg/mL or about 3.5 mg/mL, or any ranges between the recited values.

[26] The aqueous solution of [24] or [25], wherein the weight ratio of bortezomib to mannitol ranges from about 1:10 to about 1:200, e.g., about 1:20, about 1:50, about 1:100, about 1:150, or about 1:200, or any ranges between the recited values.

[27] The aqueous solution of any one of [24]-[26], wherein the weight ratio of mannitol to the sulfobutyl ether beta-cyclodextrin ranges from about 1:5 to about 5:1, e.g., about 1:3, about 1:1, about 2:1, about 5:1, or any ranges between the recited values.

[28] The aqueous solution of any one of [24]-[27], further comprising propylene glycol, benzyl alcohol, or a combination thereof.

[29] The aqueous solution of [28], wherein the propylene glycol, benzyl alcohol, or a combination thereof is present in a concentration of about 5 mg/mL to about 100 mg/mL, such as about 10 mg/mL to about 100 mg/mL, e.g., about 5 mg/mL, about 10 mg/mL, about 50 mg/mL, about 100 mg/mL, or any ranges between the recited values, such as about 5-50 mg/mL or about 10-50 mg/mL.

[30] The aqueous solution of any one of [24]-[29], further comprising a water-soluble antioxidant (e.g., a phenolic or sulfur containing antioxidant suitable for parenteral administration) in a concentration of about 0.1 mg/mL to about 10 mg/mL, such as about 0.5 mg/mL to about 10 mg/mL, e.g., about 0.5 mg/mL, about 1 mg/mL, about 2 mg/mL, about 5 mg/mL, about 10 mg/mL, or any ranges between the recited values.

[31] The aqueous solution of [30], wherein the water-soluble antioxidant comprises a sulfur containing amino acid, such as methionine, or the water-soluble antioxidant comprises monothioglycerol, sodium metabisulfite, butylated hydroxyanisole and/or butylated hydroxytoluene.

[32] The aqueous solution of any one of [24]-[31], comprising a preservative, a chelating agent, an osmotic agent, a buffer, or a combination thereof.

[33] The aqueous solution of any one of [24]-[32], which has a pH of about 1.5 to about 5.0, such as about 1.5, about 2, about 3, about 3.5, about 4, about 4.5, about 5, or any ranges between the recited values.

[34] The aqueous solution of any one of [24]-[33], which is essentially free of dissolved oxygen.

[35] The aqueous solution of any one of [24]-[34], which is storage stable.

[36] The aqueous solution of any one of [24]-[35], which is in a single-dose dosage form, e.g., packaged in an ampoule, a vial, a cartridge, a pre-filled syringe, or an intravenous bag.

[37] The aqueous solution of any one of [24]-[35], which is in a multi-dose dosage form.

[38] A method of producing the pharmaceutical composition of any one of [1]-[23], the method comprising mixing in water (1) bortezomib with (2) the polyhydric alcohol; and (3) the water-soluble antioxidant, and optional other ingredients, to form the pharmaceutical composition.

[39] The method of [38], wherein the mixing comprises:
  (i) Dissolving the polyhydric alcohol and water-soluble antioxidant, and optional other ingredients, in water to form an aqueous excipient mixture; and
  (ii) Adding bortezomib to the aqueous excipient mixture to form the pharmaceutical composition.

[40] The method of [38] or [39], further comprising sterilizing the pharmaceutical composition.

[41] The method of any one of [38]-[40], further comprising reducing dissolved oxygen in the water, aqueous excipient mixture, and/or pharmaceutical composition.

[42] The method of any one of [38]-[41], further comprising packaging or sealing the pharmaceutical composition in a container, e.g., an ampoule, a vial, a cartridge, a pre-filled syringe, or an intravenous bag.

[43] The method of [42], further comprising reducing oxygen content in the headspace of the container.

[44] A method of producing an aqueous solution suitable for pharmaceutical use (e.g., parenteral injection, such as intravenous or subcutaneous injection), the method comprising mixing bortezomib with mannitol, sulfobutyl ether beta-cyclodextrin, an optional water-soluble antioxidant, and optional other ingredients, in water to form the aqueous solution.

[45] The method of [44], wherein the optional other ingredients comprise propylene glycol, benzyl alcohol, a preservative, a chelating agent, an osmotic agent, a buffer, or a combination thereof.

[46] The method of [44] or [45], wherein the mixing comprises:
  (i) Dissolving the mannitol, sulfobutyl-ether beta-cyclodextrin, optional water-soluble antioxidant, and optional other ingredients in water to form an aqueous excipient mixture; and
  (ii) Adding bortezomib to the aqueous excipient mixture to form the aqueous solution.

[47] The method of any one of [44]-[46], further comprising sterilizing the aqueous solution.

[48] The method of any one of [44]-[47], further comprising reducing dissolved oxygen in the water, aqueous excipient mixture, and/or aqueous solution.

[49] The method of any one of [44]-[48], further comprising adjusting the pH of the aqueous solution to about 1.5 to about 5.0, such as about 1.5, about 2, about 3, about 3.5, about 4, about 4.5, about 5, or any ranges between the recited values.

[50] The method of any one of [44]-[49], further comprising packaging or sealing the aqueous solution in a container, e.g., an ampoule, a vial, a cartridge, a pre-filled syringe, or an intravenous bag.

[51] The method of [50], further comprising reducing oxygen content in the headspace of the container.

[52] The method of any one of [44]-[51], wherein the aqueous solution has a concentration of bortezomib ranging from about 0.5 mg/mL to about 3.5 mg/mL, e.g., about 1 mg/mL, about 1.5 mg/mL, about 2 mg/mL, about 2.5 mg/mL, about 3 mg/mL or about 3.5 mg/mL, or any ranges between the recited values.

[53] The method of any one of [44]-[52], wherein the weight ratio of bortezomib to mannitol in the aqueous solution ranges from about 1:10 to about 1:200, e.g., about 1:20, about 1:50, about 1:100, about 1:150, or about 1:200, or any ranges between the recited values.

[54] The method of any one of [44]-[53], wherein the weight ratio of mannitol to the sulfobutyl ether beta-cyclodextrin in the aqueous solution ranges from about 1:5 to about 5:1, e.g., about 1:3, about 1:1, about 2:1, about 5:1, or any ranges between the recited values.

[55] The method of any one of [44]-[54], comprising adding propylene glycol, benzyl alcohol, or a combination thereof to form the aqueous solution.

[56] The method of [55], wherein the propylene glycol, benzyl alcohol, or combination thereof is added in an amount of about 5 mg/mL to about 100 mg/mL, such as about 10 mg/mL to about 100 mg/mL, e.g., about 5 mg/mL, about 10 mg/mL, about 50 mg/mL, about 100 mg/mL, or any ranges between the recited values such as about 5-50 mg/mL or about 10-50 mg/mL.

[57] The method of any one of [44]-[56], comprising adding the water-soluble antioxidant to form the aqueous solution, in an amount of about 0.1 mg/mL to about 10 mg/mL, such as about 0.5 mg/mL to about 10 mg/mL, e.g., about 0.5 mg/mL, about 1 mg/mL, about 2 mg/mL, about 5 mg/mL, about 10 mg/mL, or any ranges between the recited values.

[58] The method of [57], wherein the water-soluble antioxidant comprises a sulfur containing amino acid, such as methionine, or the water-soluble antioxidant comprises monothioglycerol, sodium metabisulfite, butylated hydroxyanisole and/or butylated hydroxytoluene.

[59] The aqueous solution produced by any of the methods according to [44]-[58]. [60] The aqueous solution of [59], which is storage stable.

[61] A lyophilized powder composition prepared from the pharmaceutical composition of any one of [1]-[23] or the aqueous solution of any one of [24]-[37] and [59]-[60].

[62] A reconstituted solution prepared from the lyophilized powder composition of [61].

[63] A method of stabilizing a liquid pharmaceutical composition comprising bortezomib, the method comprising mixing in water (1) bortezomib; (2) a polyhydric alcohol; and (3) a water-soluble antioxidant; and optional other ingredients, to form the pharmaceutical composition.

[64] The method of [63], wherein the mixing comprises:
  (i) Dissolving the polyhydric alcohol and water-soluble antioxidant, and optional other ingredients, in water to form an aqueous excipient mixture; and
  (ii) Adding bortezomib to the aqueous excipient mixture to form the pharmaceutical composition.

[65] The method of [63] or [64], further comprising sterilizing the pharmaceutical composition.

[66] The method of any one of [63]-[65], further comprising reducing dissolved oxygen in the water and/or pharmaceutical composition.

[67] The method of any one of [63]-[66], further comprising packaging or sealing the pharmaceutical composition in a container, e.g., an ampoule, a vial, a cartridge, a pre-filled syringe, or an intravenous bag.

[68] The method of [67], further comprising reducing oxygen content in the headspace of the container.

[69] The method of any one of [63]-[68], wherein the pharmaceutical composition has bortezomib in a concentration ranging from about 0.5 mg/mL to about 3.5 mg/mL, e.g., about 1 mg/mL, about 1.5 mg/mL, about 2 mg/mL, about 2.5 mg/mL, about 3 mg/mL or about 3.5 mg/mL, or any ranges between the recited values.

[70] The method of any one of [63]-[69], wherein the weight ratio of bortezomib to the polyhydric alcohol in the pharmaceutical composition ranges from about 1:10 to about 1:200, e.g., about 1:20, about 1:50, about 1:100, about 1:150, or about 1:200, or any ranges between the recited values.

[71] The method of any one of [63]-[70], wherein the polyhydric alcohol comprises mannitol.

[72] The method of any one of [63]-[71], wherein the optional other ingredients comprise a water-soluble cyclodextrin.

[73] The method of [72], wherein the weight ratio of the polyhydric alcohol to the water-soluble cyclodextrin in the pharmaceutical composition ranges from about 1:5 to about 5:1, e.g., about 1:3, about 1:1, about 2:1, about 5:1, or any ranges between the recited values.

[74] The method of [72] or [73], wherein the water-soluble cyclodextrin comprises hydroxypropyl β-cyclodextrin (HPβCD), sulfobutyl ether β-cyclodextrin (SBEβCD), or a combination thereof.

[75] The method of any one of [63]-[74], wherein the optional other ingredients comprise propylene glycol, benzyl alcohol, or a combination thereof.

[76] The pharmaceutical composition of [75], wherein the propylene glycol, benzyl alcohol, or combination thereof is added to the pharmaceutical composition in an amount of about 5 mg/mL to about 100 mg/mL, such as about 10 mg/mL to about 100 mg/mL, e.g., about 5 mg/mL, about 10 mg/mL, about 50 mg/mL, about 100 mg/mL, or any ranges between the recited values such as about 5-50 mg/mL or about 10-50 mg/mL.

[77] The method of any one of [63]-[76], wherein the water-soluble antioxidant in the pharmaceutical composition is in an amount of about 0.1 mg/mL to about 10 mg/mL, such as about 0.5 mg/mL to about 10 mg/mL, e.g., about 0.5 mg/mL, about 1 mg/mL, about 2 mg/mL, about 5 mg/mL, about 10 mg/mL, or any ranges between the recited values.

[78] The method of [77], wherein the water-soluble antioxidant comprises a sulfur containing amino acid, such as methionine, or the water-soluble antioxidant comprises monothioglycerol, sodium metabisulfite, butylated hydroxyanisole and/or butylated hydroxytoluene.

[79] The method of any one of [63]-[78], further comprising adjusting the pH of the pharmaceutical composition to about 1.5 to about 5.0, such as about 1.5, about 2, about 3, about 3.5, about 4, about 4.5, about 5, or any ranges between the recited values.

[80] The method of any one of [63]-[79], wherein the optional other ingredients comprise a preservative, a chelating agent, an osmotic agent, a buffer, or a combination thereof.

[81] A method of stabilizing an aqueous solution comprising bortezomib which is suitable for pharmaceutical use (e.g., parenteral injection, such as intravenous or subcutaneous injection), the method comprising mixing bortezomib with mannitol, sulfobutyl ether beta-cyclodextrin, an optional water-soluble antioxidant, and optional other ingredients, in water to form the aqueous solution.

[82] The method of [82], wherein the optional other ingredients comprise a preservative, a chelating agent, an osmotic agent, a buffer, or a combination thereof.

[83] The method of [81] or [82], wherein the mixing comprises:
(i) Dissolving the mannitol, sulfobutyl ether beta-cyclodextrin, optional water-soluble antioxidant, and optional other ingredients in water to form an aqueous excipient mixture; and
(ii) Adding bortezomib to the aqueous excipient mixture to form the aqueous solution.

[84] The method of any one of [81]-[83], further comprising sterilizing the aqueous solution.

[85] The method of any one of [81]-[84], further comprising reducing dissolved oxygen in the water, aqueous excipient mixture, and/or aqueous solution.

[86] The method of any one of [81]-[85], further comprising adjusting the pH of the aqueous solution to about 1.5 to about 5.0, such as about 1.5, about 2, about 3, about 3.5, about 4, about 4.5, about 5, or any ranges between the recited values.

[87] The method of any one of [81]-[86], further comprising packaging or sealing the pharmaceutical composition in a container, e.g., an ampoule, a vial, a cartridge, a pre-filled syringe, or an intravenous bag.

[88] The method of [87], further comprising reducing oxygen content in the headspace of the container.

[89] The method of any one of [81]-[88], wherein the aqueous solution has a concentration of bortezomib ranging from about 0.5 mg/mL to about 3.5 mg/mL, e.g., about 1 mg/mL, about 1.5 mg/mL, about 2 mg/mL, about 2.5 mg/mL, about 3 mg/mL or about 3.5 mg/mL, or any ranges between the recited values.

[90] The method of any one of [81]-[89], wherein the weight ratio of bortezomib to mannitol in the aqueous solution ranges from about 1:10 to about 1:200, e.g., about 1:20, about 1:50, about 1:100, about 1:150, or about 1:200, or any ranges between the recited values.

[91] The method of any one of [81]-[90], wherein the weight ratio of mannitol to the sulfobutyl ether beta-cyclodextrin in the aqueous solution ranges from about 1:5 to about 5:1, e.g., about 1:3, about 1:1, about 2:1, about 5:1, or any ranges between the recited values.

[92] The method of any one of [81]-[91], comprising adding to the aqueous solution propylene glycol, benzyl alcohol, or a combination thereof in an amount of about 5 mg/mL to about 100 mg/mL, such as about 10 mg/mL to about 100 mg/mL, e.g., about 5 mg/mL, about 10 mg/mL, about 50 mg/mL, about 100 mg/mL, or any ranges between the recited values such as about 5-50 mg/mL or about 10-50 mg/mL.

[93] The method of any one of [81]-[92], comprising adding to the aqueous solution the water-soluble antioxidant in a concentration of about 0.1 mg/mL to about 10 mg/mL, such as about 0.5 mg/mL to about 10 mg/mL, e.g., about 0.5 mg/mL, about 1 mg/mL, about 2 mg/mL, about 5 mg/mL, about 10 mg/mL, or any ranges between the recited values.

[94] The method of [93], wherein the water-soluble antioxidant comprises a sulfur containing amino acid, such as methionine, or the water-soluble antioxidant comprises monothioglycerol, sodium metabisulfite, butylated hydroxyanisole and/or butylated hydroxytoluene.

[95] A pharmaceutical composition according to Formulation I-1, I-2, I-3, II-1, II-2, II-3, II-4, III-1, III-2, IV-1, IV-2, IV-3, V-1, V-2, V-3, V-4, or V-5 in the Examples section or AF1-AF16 as described herein.

[96] A method of inhibiting proteasome function in a subject in need thereof, the method comprising administering to the subject an effective amount of any of the pharmaceutical compositions of [1]-[23], [100]-[119], and [95], the aqueous solution of claims [24]-[37], [59], and [60], and the reconstituted solution of claim [62].

[97] A method of treating cancer in a subject in need thereof, the method comprising administering to the subject a therapeutically effective amount of any of the pharmaceutical compositions of [1]-[23], [100]-[119], and [95], the aqueous solution of claims [24]-[37], [59], and [60], and the reconstituted solution of claim

[62]. [98] The method of [97], wherein the cancer is multiple myeloma and/or mantle cell lymphoma.

[99] A method of treating a disease or disorder for which bortezomib is indicated for or known to be beneficial, the method comprising administering to a subject in need thereof a therapeutically effective amount of any of the pharmaceutical compositions of [1]-[23], [100]-[119], and [95], the aqueous solution of claims [24]-[37], [59], and [60], and the reconstituted solution of claim [62].

[100] A pharmaceutical composition comprising (1) bortezomib; (2) mannitol; and (3) methionine.

[101] A pharmaceutical composition comprising (1) bortezomib; (2) mannitol; (3) methionine; and (4) an optional chelating agent (e.g., EDTA).

[102] A pharmaceutical composition comprising (1) bortezomib; (2) mannitol; (3) methionine; and (4) an optional buffer (e.g., glycine).

[103] A pharmaceutical composition comprising (1) bortezomib; (2) mannitol; (3) methionine; and (4) EDTA.

[104] A pharmaceutical composition comprising (1) bortezomib; (2) mannitol; (3) methionine; and (4) glycine.

[105] A pharmaceutical composition comprising (1) bortezomib; (2) mannitol; (3) methionine; (4) EDTA and (5) glycine.

[106] The pharmaceutical composition according to any of [100]-[105], wherein the pharmaceutical composition is in a liquid form.

[107] The pharmaceutical composition according to any of [100]-[106], wherein bortezomib is in a concentration ranging from about 0.5 mg/mL to about 3.5 mg/mL, e.g., about 1 mg/mL, about 1.5 mg/mL, about 2 mg/mL, about 2.5 mg/mL, about 3 mg/mL or about 3.5 mg/mL, or any ranges between the recited values.

[108] The pharmaceutical composition according to any of [100]-[107], wherein the weight ratio of bortezomib to mannitol ranges from about 1:10 to about 1:200, e.g., about 1:20, about 1:50, about 1:100, about 1:150, or about 1:200, or any ranges between the recited values.

[109] The pharmaceutical composition according to any of [100]-[108], wherein mannitol is in an amount of about 50 mg/mL to about 300 mg/mL, such as about 60 mg/mL, about 80 mg/mL, about 100 mg/mL, about 125 mg/mL, about 150 mg/mL, about 200 mg/mL, about 250 mg/mL, or about 300 mg/mL, or any ranges between the recited values.

[110] The pharmaceutical composition according to any of [100]-[109], wherein methionine is in an amount of about 0.1 mg/mL to about 10 mg/mL, such as about 0.5 mg/mL to about 10 mg/mL, or about 0.1 mg/mL to about 5 mg/mL, e.g., about 0.5 mg/mL, about 1 mg/mL, about 2 mg/mL, about 3 mg/mL, about 4 mg/mL, about 5 mg/mL, about 10 mg/mL, or any ranges between the recited values.

[111] The pharmaceutical composition according to any of [100]-[110], comprising EDTA at a concentration of about 0.01 mg/mL to about 10 mg/mL, such as about 0.01 mg/mL, about 0.1 mg/mL, about 0.5 mg/mL, about 1 mg/mL, about 2 mg/mL, about 5 mg/mL, about 10 mg/mL, or any ranges between the recited values such as about 0.1-1 mg/mL.

[112] The pharmaceutical composition according to any of [100]-[111], having a pH of about 1.5 to about 5.0, such as about 1.5, about 2, about 3, about 3.5, about 4, about 4.5, about 5, or any ranges between the recited values, such as about 2 to about 4.5, such as about 3.5.

[113] The pharmaceutical composition according to any of [100]-[112], which is a ready-to-use aqueous solution, wherein the aqueous solution comprises water in an amount of greater than 50% by weight, e.g., about 60%, about 70%, about 80%, about 85%, about 90%, about 95%, or any ranges between the recited values, such as about 60-85%, about 60-95%, about 70-80%, about 70-90%, etc.

[114] The pharmaceutical composition of any one of [100]-[113], wherein the pharmaceutical composition further comprises propylene glycol, benzyl alcohol, or a combination thereof.

[115] The pharmaceutical composition of [114], wherein the propylene glycol, benzyl alcohol, or combination thereof is present in a concentration of about 5 mg/mL to about 100 mg/mL, such as about 10 mg/mL to about 100 mg/mL, e.g., about 5 mg/mL, about 10 mg/mL, about 50 mg/mL, about 100 mg/mL, or any ranges between the recited values such as about 10-50 mg/mL or about 5-50 mg/mL.

[116] The pharmaceutical composition of any one of [100]-[115], which is essentially free of dissolved oxygen.

[117] The pharmaceutical composition of any one of [100]-[116], which is storage stable.

[118] The pharmaceutical composition of any one of [100]-[117], which is in a single-dose dosage form, e.g., packaged in an ampoule, a vial, a cartridge, a pre-filled syringe, an intravenous bag.

[119] The pharmaceutical composition of any one of [100]-[118], which is in a multi-dose dosage form.

It is to be understood that both the foregoing summary and the following detailed description are exemplary and explanatory only, and are not restrictive of the invention herein.

BRIEF DESCRIPTION OF THE DRAWINGS

FIG. 1 shows a sample HPLC trace using the HPLC method described herein. The sample HPLC trace shows the peaks of bortezomib (BTZM), impurities A, C1, C2, D, labeled as IMP A, C1, C2, and D, respectively, and the impurity having a relative retention time of about 0.87-0.88.

DETAILED DESCRIPTION

Bortezomib is an N-protected dipeptidyl boronic acid. It structurally shares the disadvantage with other peptidyl boronic acids and esters that it undergoes fast degradation under standard conditions of manufacturing and storage, especially in an aqueous environment. Boronic acids and esters tend to form anhydrides, including cyclic anhydrides referred to as "boroxines," during dehydration. Boronic acids and esters also tend to oxidize in air, which can severely limit their shelf life. Thus, bortezomib typically is difficult to formulate into a stable therapeutic product in liquid forms, particularly in aqueous media. One conventional method of increasing the stability of bortezomib involves combining the boronic acid with a sugar or other compound having two or more hydroxyl groups separated by at least two connecting atoms (i.e. C, N, S or O). It is reported that bortezomib forms a boronate ester with such a di-hydroxyl compound, and that this ester is more stable to air and to dehydration than bortezomib alone. Nevertheless, in order to be viable as a commercial drug product, a mixture of bortezomib and such a di-hydroxyl compound must be subjected to lyophilization to remove the solvent, providing an essentially dry form containing the bortezomib, the dihydroxyl compound and/or an ester of the bortezomib and the dihydroxyl compound. This sugar stabilization method has been implemented in the formulations of the currently available commercial products and sold under the trade name of VELCADE® (Millennium Pharmaceuticals, Inc.; Cambridge, Mass., USA) and similarly in two other Bortezomib for Injection products marketed by Fresenius Kabi USA Inc., and Dr. Reddy's Laboratories, Inc. Nevertheless, all three products are available only in the dry form as a lyophilized powder. In each case, the lyophilized powder products must be reconstituted by combining the lyophilized powder with 0.9% sodium chloride saline, to provide an injectable solution for patient administration. Furthermore, regardless of which boronate esters it formed with in the dry form, the reconstituted solution of bortezomib is stable only for up to 8 hours of preparation.

The difficulties in formulating bortezomib formulations are also described, for example in WO2010/089768, 2011/0178470A1, US2012/0322763A1, U.S. Pat. No. 8,263,578, US20170035831A1, and US20180110822A1. Despite of various approaches to stabilize bortezomib formulations, it remains a challenge to produce a ready-to-use bortezomib formulations, such as an aqueous composition containing bortezomib, that is stable for an extended period of time and that can be administered without further handling and manipulation, such as reconstitution and dilution of such cytotoxic drug.

Chemically, bortezomib is susceptible to two major degradation pathways, oxidation and hydrolysis. In order to maintain proper stability to be commercially viable, the finished drug products of bortezomib on the market were made into the dry form by lyophilization process. Various studies in the literature indicate that bortezomib is extremely unstable in aqueous environment, especially in aqueous solutions. The reconstituted solution of bortezomib lyophilized powder is so unstable that the reconstituted solution is stable for only up to 8 hours.

Stabilization of such highly unstable molecules is extremely difficult as demonstrated by various common approaches of pharmaceutical formulation, such as lyophilization to make it into a solid state or using non-aqueous solvents or vehicles.

As described herein, it was surprisingly discovered that the use of a combination of different functional excipients, such as antioxidant and different polyhydroxy excipients, is able to effectively slow down the degradation of bortezomib in aqueous environment. Accordingly, in various embodiments, the present disclosure provides compositions of bortezomib comprising bortezomib or its pharmaceutically acceptable forms, at least one or more stabilizers selected from polyhydroxy containing compounds and one or more antioxidants, wherein the compositions of bortezomib are typically storage stable. In some embodiments, the compositions herein can also include other formulation modifiers, such as chelating agents, antimicrobial preservatives, buffer agents, tonicity agents, and inert gases, etc. These formulation modifiers can be added or used to further ensure that such aqueous compositions be clinically and commercially viable as a parenteral drug. As would be understood by those skilled in the art, the ingredients of the pharmaceutical compositions described herein may have multiple functions. For example, benzyl alcohol can be used to dissolve bortezomib in preparing some of the pharmaceutical compositions herein, but can also have an effect as a preservative. It should be understood that when a specific ingredient in a list is followed by a generic formulation ingredient such as a chelating agent, preservative, etc., the specific ingredient and the generic formulation ingredient should not be understood as mutually exclusive.

Without wishing to be bound by theories, the compositions herein typically include various ingredients that provide multiple protective effects additively or synergistically against the potential degradation of bortezomib in aqueous environment. Degradation of bortezomib that occurs in liquid forms is therefore effectively retarded and bortezomib compositions become stable in an essentially organic solvent free aqueous media or in a dried form made from such compositions. While the embodiments described herein are more specifically directed to bortezomib formulations, it is also contemplated that other boronic acid compounds can be stabilized similarly. Thus, in some embodiments, aqueous formulations of other boronic acid compounds such as dipeptidyl boronic acids are also provided herein. For example, any embodiments described herein for bortezomib can also be applicable to boronic acid compounds in general, in particular, N-protected dipeptidyl boronic acids.

The composition of bortezomib herein typically exhibits extended storage stability, both physically and chemically. A "storage stable" bortezomib composition, as used herein, should be understood as such that when stored at room temperature or at 40° C. for 1 month or longer, such as for 3 months or longer, the bortezomib composition has the bortezomib content maintained above 90% of the initial amount and the total degradation products formed about 10% or less. In some embodiments, the storage stable bortezomib composition, when stored at 40° C. for 1 month or longer, such as for 3 months or longer, has the bortezomib content maintained above 90% of the initial amount and the total degradation products formed about 10% or less. The content of bortezomib and degradation products can be measured using the HPLC methods described herein.

The composition of bortezomib herein is typically essentially free of an organic solvent. For example, in any of the embodiments described herein, unless otherwise contrary from context, the pharmaceutical composition (e.g., aqueous solution) herein can be essentially free of an organic solvent, such as a glycol (e.g., propylene glycol). For example, in some embodiments, the pharmaceutical composition (e.g., aqueous solution) herein can be free of propylene glycol or have less than 50 mg/mL of propylene glycol. In some embodiments, the pharmaceutical composition (e.g., aqueous solution) herein can be free of benzyl alcohol or have less than 50 mg/mL of benzyl alcohol. In some embodiments, the pharmaceutical composition (e.g., aqueous solution) herein can be free of propylene glycol and benzyl alcohol or have less than 50 mg/mL of propylene glycol and benzyl alcohol. However, as described herein, in some embodiments, the pharmaceutical composition (e.g., aqueous solution) herein can also include propylene glycol, benzyl alcohol, or a combination thereof, in an amount as described herein.

In any of the embodiments described herein, unless otherwise contrary from context, the pharmaceutical composition (e.g., aqueous solution) herein can be a ready-to-use formulation, which can be used directly without further handling such as reconstitution and/or dilution. The ready-to-use pharmaceutical composition (e.g., aqueous solution) herein typically comprises water in an amount of greater than 50% by weight, e.g., about 60%, about 70%, about 80%, about 85%, about 90%, about 95%, or any ranges between the recited values, such as about 60-85%, about 60-95%, about 70-80%, about 70-90%, etc. The ready-to-use formulation herein typically can be prepared without a lyophilization and/or reconstitution step. However, as would be understood by those skilled in the art, a lyophilized bortezomib material (such as those with mannitol, boric acid, tromethamine, etc.) can also be used for preparing the pharmaceutical composition or aqueous solution herein. As described herein, the ready-to-use formulation herein, once prepared, can be stable in a liquid state, which allows storage and multiple uses without any further manipulations such as a lyophilization and/or reconstitution step. In some particular embodiments, the ready-to-use formulation herein is in a multi-dose dosage form, which can be packaged in any suitable container, and can be storage stable for an extended period of time, e.g., 1 month, 3 months, or longer, at about 5° C. or about 25° C. after multiple accesses.

Pharmaceutical Compositions Comprising Bortezomib

The present disclosure generally relates to pharmaceutical compositions, such as stable liquid compositions, comprising bortezomib or its pharmaceutically acceptable form. Typically, the pharmaceutical composition herein, such as a stable liquid composition, comprises at least one pharmaceutically acceptable additive which structurally contains multiple hydroxyl groups, such as polyhydric alcohols or sugar alcohols, water-soluble derivative of cyclodextrins, or a combination of both, and optionally one or more water-soluble antioxidants, such as sulfur dioxide antioxidants or sulfur-containing amino acids. As used herein, an ingredient can be characterized as a "water-soluble" ingredient, even if the ingredient does not have unlimited solubility in water. It is sufficient that the ingredient can be dissolved in water or the aqueous solution/pharmaceutical composition described herein at the recited concentration. While the pharmaceutical compositions herein typically include such ingredient(s) in a water-soluble amount, it is also contemplated that one or more of such ingredients may be included in some embodiments of the pharmaceutical composition herein in excess of its respective solubility in the pharmaceutical composition. Typically, the pharmaceutical composition herein can include one or more polyhydroxy compounds described herein, wherein the weight ratio of bortezomib to the polyhydroxy compound is between about 1:10 to about 1:200, preferably from about 1:20 to about 1:150. Although optional, the pharmaceutical composition herein typically also have one or more water-soluble antioxidants described herein, such as have at least one sulfur containing antioxidant (e.g., such as a sulfur containing amino acid).

In some embodiments, the pharmaceutical composition herein comprises (1) bortezomib; (2) a polyhydric alcohol; and optionally (3) a water-soluble antioxidant, wherein the pharmaceutical composition is in a liquid form. The pharmaceutical composition is typically a ready-to-use aqueous solution, which typically comprises water in an amount of greater than 50% by weight, e.g., about 60%, about 70%, about 80%, about 85%, about 90%, about 95%, or any ranges between the recited values, such as about 60-85%, about 60-95%, about 70-80%, about 70-90%, etc.

Bortezomib in a non-aqueous environment may be relatively more stable than in an aqueous environment. However, non-aqueous bortezomib formulations require the use of organic solvent(s), which can cause various adverse effects when injected into a subject. For example, Laurent A. et al. discloses that certain organic solvents such as propylene glycol may have marked cardiovascular toxicity, see PDA journal of pharmaceutical science and technology, 54(6):456-69, November 2000. In contrast, the pharmaceutical compositions herein are typically substantially aqueous and can avoid using any of the organic solvents typically used in such non-aqueous bortezomib formulations. In any of the embodiments described herein, unless otherwise contrary from context, the pharmaceutical composition or aqueous solution herein can also be essentially free of an organic solvent, such as a glycol (e.g., propylene glycol).

In some embodiments, the pharmaceutical composition herein (e.g., any of those described in [1]-[37], [59], [60], [62] and [100]-[119] in the Brief Summary section herein, or any of AF1 to AF16 (described herein below), as applicable) can be characterized as being free, essentially free, or substantially free of an organic solvent, such as with less than 10% weight to volume ("w/v"), less than 5% w/v, less than 4% w/v, less than 3% w/v, less than 2% w/v, less than 1% w/v, less than 0.5% w/v, or a non-detectable amount of the organic solvent. As would be understood by those skilled in the art, a 1% w/v of an ingredient in a solution means 10 mg of the ingredient in 1 mL of the solution.

In some embodiments, the pharmaceutical composition herein (e.g., any of those described in [1]-[37], [59], [60], [62] and [100]-[119] in the Brief Summary section herein, or any of AF1 to AF16, as applicable) can be characterized as being free, essentially free, or substantially free of any one or more organic solvent selected from propylene glycol, polyethylene glycols, ethanol, dimethyl sulfoxide, N-methyl-2-pyrrolidone, glycofurol, Solketal, glycerol formal, acetone, tetrahydrofurfuryl alcohol, diglyme, dimethyl isosorbide, and ethyl lactate, such as with less than 10% w/v, less than 5% w/v, less than 4% w/v, less than 3% w/v, less than 2% w/v, less than 1% w/v, less than 0.5% w/v, or a non-detectable amount of the organic solvent. For the avoidance of doubt, when it is said that a composition is free of any one or more ingredient (e.g., an organic solvent) selected from A, B, and C, or that a composition is free of A, B, C, and combinations thereof, A, B, and C, either singularly or in any combination, is not present in the composition in a detectable amount. When it is said that a composition is essentially free or substantially free of any one or more ingredient (e.g., an organic solvent) selected from A, B, and C, or that a composition is essentially free or substantially free of A, B, C, and combinations thereof, the combined amount of A, B, and C that may be present in the composition should not exceed the specified amount, such as less than 10% w/v. Similar expressions in other contexts should be understood similarly.

In some embodiments, the pharmaceutical composition (e.g., any of those described in [1]-[37], [59], [60], [62] and [100]-[119] in the Brief Summary section herein, or any of AF1 to AF16, as applicable) can be characterized as being free, essentially free, or substantially free of any one or more glycol solvent, such as with less than 10% w/v, less than 5% w/v, less than 4% w/v, less than 3% w/v, less than 2% w/v, less than 1% w/v, less than 0.5% w/v, or a non-detectable amount of the glycol solvent.

In some embodiments, the pharmaceutical composition herein (e.g., any of those described in [1]-[37], [59], [60], [62] and [100]-[119] in the Brief Summary section herein, or any of AF1 to AF16, as applicable) can be free, essentially free, or substantially free of propylene glycol, such as having less than 50 mg/mL of propylene glycol.

In some embodiments, the pharmaceutical composition (e.g., any of those described in [1]-[37], [59], [60], [62] and [100]-[119] in the Brief Summary section herein, or any of AF1 to AF16, as applicable) can be characterized as being free, essentially free, or substantially free of any one or more alcohol solvent, such as with less than 10% w/v, less than 5% w/v, less than 4% w/v, less than 3% w/v, less than 2% w/v, less than 1% w/v, less than 0.5% w/v, or a non-detectable amount of the alcohol solvent.

In some embodiments, the pharmaceutical composition herein (e.g., any of those described in [1]-[37], [59], [60], [62] and [100]-[119] in the Brief Summary section herein, or any of AF1 to AF16, as applicable) can be free, essentially free, or substantially free of benzyl alcohol, such as having less than 50 mg/mL of benzyl alcohol. In some embodiments, the pharmaceutical composition herein (e.g., any of those described in [1]-[37], [59], [60], [62] and [100]-[119] in the Brief Summary section herein, or any of AF1 to AF16, as applicable) can be free, essentially free, or substantially free of ethanol, such as having less than 50 mg/mL of ethanol.

In some embodiments, the pharmaceutical composition (e.g., any of those described in [1]-[37], [59], [60], [62] and [100]-[119] in the Brief Summary section herein, or any of AF1 to AF16, as applicable) can be characterized as being free, essentially free, essentially free, or substantially free of propylene glycol, benzyl alcohol, and a combination thereof, such as with less than 10% w/v, less than 5% w/v, less than 4% w/v, less than 3% w/v, less than 2% w/v, less than 1% w/v, less than 0.5% w/v, or a non-detectable amount of propylene glycol, benzyl alcohol, and combination thereof.

However, as described herein, in some embodiments, the pharmaceutical composition herein (e.g., any of those described in [1]-[37], [59], [60], [62] and [100]-[119] in the Brief Summary section herein, or any of AF1 to AF16, as applicable) can also include propylene glycol, benzyl alcohol, or a combination thereof, in an amount as described herein, typically less than 100 mg/mL. In some embodiments, the pharmaceutical composition herein (e.g., any of those described in [1]-[37], [59], [60], [62] and [100]-[119] in the Brief Summary section herein, or any of AF1 to AF16, as applicable) can include propylene glycol, benzyl alcohol, or a combination thereof, in an amount such as about 5 mg/mL to about 100 mg/mL, such as about 10 mg/mL to about 100 mg/mL, e.g., about 5 mg/mL, about 10 mg/mL, about 50 mg/mL, about 100 mg/mL, or any ranges between the recited values such as about 5-50 mg/mL or about 10-50 mg/mL.

A typical pharmaceutical composition herein (e.g., any of those described in [1]-[37], [59], [60], [62] and [100]-[119] in the Brief Summary section herein, or any of AF1 to AF16, as applicable) can comprise bortezomib formulated at a concentration of about 0.5 mg/mL to about 3.5 mg/mL, e.g., about 1 mg/mL, about 1.5 mg/mL, about 2 mg/mL, about 2.5 mg/mL, about 3 mg/mL or about 3.5 mg/mL, or any ranges between the recited values, such as about 1-3 mg/mL or 1.5-3.5 mg/mL etc. In some embodiments, the pharmaceutical composition herein (e.g., any of those described in [1]-[37], [59], [60], [62] and [100]-[119] in the Brief Summary section herein, or any of AF1 to AF16, as applicable) can comprise bortezomib formulated at a concentration of from about 1 mg/mL to about 3.0 mg/mL. It should be understood that the unit "mg/mL" refers to the weight of an ingredient, such as bortezomib, in the volume of the final composition. The concentration of bortezomib in a given composition can be calculated based on the bortezomib used for preparing the composition and/or can be measured by HPLC, e.g., as shown in the Examples section. Bortezomib in the compositions herein may exist in a cyclic anhydride form, monomeric boronic acid form, a salt form, or in equilibrium with other forms, such as an ester formed with an excipient. The amount of bortezomib in the compositions herein should be understood as referring to the total amount of bortezomib expressed as the equivalent weight based on the monomeric boronic acid.

In some embodiments, the pharmaceutical composition herein (e.g., any of those described in [1]-[2], [4]-[24], [26]-[37], [59], [60], [62] and [100]-[119] in the Brief Summary section herein, or any of AF1 to AF16, as applicable) can comprise bortezomib formulated at a concentration of more than 3.5 mg/mL, such as more than 4 mg/mL, more than 5 mg/mL, etc. and up to the maximum solubility in the pharmaceutical composition. Typically, pharmaceutical compositions with high bortezomib concentrations can be a ready-to-dilute formulation, which can be diluted to a desired concentration prior to use.

The polyhydric alcohol that can be included in the pharmaceutical composition is not particularly limited. Useful polyhydric alcohols for the pharmaceutical compositions herein can typically have a formula of $HOCH_2(CHOH)_nCH_2OH$, wherein n can be an integer of 0-30. In any of the embodiments described herein, unless otherwise specified or obviously contrary from context, the polyhydric alcohol in the pharmaceutical composition herein can comprise, consist essentially of, or consist of mannitol. In some preferred embodiments, the pharmaceutical composition comprises mannitol. For example, in some embodiments, the pharmaceutical composition herein can comprise (1) bortezomib; (2) mannitol; and optionally (3) a water-soluble antioxidant (e.g., described herein). In any of the embodiments described herein, unless otherwise specified or obviously contrary from context, the pharmaceutical composition herein can comprise (1) bortezomib; (2) mannitol; and (3) a water-soluble antioxidant (e.g., described herein, such as methionine), and optionally other ingredients. For example, in some embodiments, the pharmaceutical composition herein can comprise (1) bortezomib; (2) mannitol; and (3) methionine. In some embodiments, the pharmaceutical composition herein can comprise (1) bortezomib; (2) mannitol; (3) methionine; and (4) an optional chelating agent (e.g., EDTA). In some embodiments, the pharmaceutical composition herein can comprise (1) bortezomib; (2) mannitol; (3) methionine; and (4) an optional buffer (e.g., glycine). In some embodiments, the pharmaceutical composition herein can comprise (1) bortezomib; (2) mannitol; (3) methionine; and (4) EDTA. In some embodiments, the pharmaceutical composition herein can comprise (1) bortezomib; (2) mannitol; (3) methionine; and (4) glycine. In some embodiments, the pharmaceutical composition herein can comprise (1) bortezomib; (2) mannitol; (3) methionine; (4) EDTA and (5) glycine. The amounts of bortezomib, mannitol, and water-soluble antioxidant (e.g., methionine), as well as that of the optional ingredients such as the optional chelating agent (e.g., EDTA) and optional buffer (e.g., glycine), include any of those described herein in any combinations.

The amount of polyhydric alcohol in the pharmaceutical composition herein is typically in excess of the amount of bortezomib. In some preferred embodiments, the pharmaceutical composition herein (e.g., any of those described in [1]-[37], [59], [60], [62] and [100]-[119] in the Brief Summary section herein, or any of AF1 to AF16, as applicable) can be characterized by a weight ratio of bortezomib to the polyhydric alcohol ranging from about 1:10 to about 1:200, e.g., about 1:20, about 1:50, about 1:100, about 1:150, or about 1:200, or any ranges between the recited values. In some preferred embodiments, the pharmaceutical composition herein (e.g., any of those described in [1]-[37], [59], [60], [62] and [100]-[119] in the Brief Summary section herein, or any of AF1 to AF16, as applicable) can be characterized by a concentration of the polyhydric alcohol ranging from about 40 mg/mL to about 200 mg/mL, such as about 50 mg/mL, about 75 mg/mL, about 100 mg/mL, about 150 mg/mL, about 200 mg/mL, or any range between the recited values, such as about 50-150 mg/mL. For example, in some embodiments, the pharmaceutical composition herein (e.g., any of those described in [1]-[37], [59], [60], [62] and [100]-[119] in the Brief Summary section herein, or any of AF1 to AF16, as applicable) can comprise mannitol, wherein the weight ratio of bortezomib to mannitol can range from about 1:10 to about 1:200, e.g., about 1:20, about 1:50, about 1:100, about 1:150, or about 1:200, or any ranges between the recited values. In some preferred embodiments, the pharmaceutical composition herein (e.g., any of those described in [1]-[37], [59], [60], [62] and [100]-[119] in the Brief Summary section herein, or any of AF1 to AF16, as applicable) can comprise mannitol, wherein the weight ratio of bortezomib to mannitol can range from about 1:20 to about 1:200, such as from about 1:50 to about 1:200, from about 1:50 to about 1:150, from about 1:100 to about 1:200, etc. In some embodiments, the pharmaceutical composition herein can be characterized by a weight ratio of bortezomib to mannitol lower than 1:200, such as about 1:250, about 1:300, about 1:400, or even lower. In some preferred embodiments, the pharmaceutical composition herein (e.g., any of those described in [1]-[37], [59], [60], [62] and [100]-[119] in the Brief Summary section herein, or any of AF1 to AF16, as applicable) can comprise mannitol, wherein the concentration of mannitol ranges from about 40 mg/mL to about 200 mg/mL, such as about 50 mg/mL, about 75 mg/mL, about 100 mg/mL, about 150 mg/mL, about 200 mg/mL, or any range between the recited values, such as about 50-150 mg/mL. Without wishing to be bound by theories, it is believed that the higher content of polyhydric alcohol such as mannitol in the pharmaceutical composition herein is one of the factors that leads to the stabilization of bortezomib in an aqueous solution. As shown in Example 6 of the Examples section herein, it was unexpectedly found that with bortezomib concentration at 1 mg/mL, aqueous solutions with mannitol concentrations at 40 mg/mL up to 100 mg/mL are more stable compared to similar formulations with mannitol concentrations at 20 mg/mL or below. This result is in contrast to those observed in WO2018/164513, which shows that increasing mannitol content has essentially no effect on the stability of the formulations described therein.

In some embodiments, the pharmaceutical composition herein can comprise a water-soluble cyclodextrin. Without wishing to be bound by theories, it is believed that the presence of a water-soluble cyclodextrin can provide at least additive effect to that of the polyhydric alcohol in stabilizing bortezomib in an aqueous environment.

In some embodiments, the pharmaceutical composition can comprise (1) bortezomib; (2) a polyhydric alcohol; (3) a water-soluble cyclodextrin; and optionally (4) a water-soluble antioxidant (e.g., as described herein), wherein the polyhydric alcohol, water-soluble cyclodextrin, and optional water-soluble antioxidant, and the amount/concentration thereof, include any of those described herein in any combinations. For example, in some embodiments, the pharmaceutical composition can comprise (1) bortezomib; (2) mannitol; (3) a water-soluble cyclodextrin; and optionally (4) a water-soluble antioxidant (e.g., as described herein).

Cyclodextrins (CDs) are groups of cyclic oligosaccharides which have been shown to be useful for formulation various drugs. CDs are cyclic oligosaccharides composed of several D-glucose units linked by α-(1,4) bonds. This cyclic configuration provides a hydrophobic internal cavity and gives the CDs a truncated cone shape. Many hydroxyl groups are situated on the edges of the ring which make the CDs both lipophilic and soluble in water.

The terms "cyclodextrin" or "CD" unless otherwise specified herein, refer generally to a parent or derivatized cyclic oligosaccharide containing a variable number of (α-1,4)-linked D-glucopyranoside units. Each cyclodextrin glucopyranoside subunit has secondary hydroxyl groups at the 2 and 3 positions and a primary hydroxyl group at the 6-position. The terms "parent", "underivatized", or "inert", cyclodextrin refer to a cyclodextrin containing D-glucopyranoside units having the basic formula C6H12O6 and a glucose structure without any additional chemical substitutions (e.g., α-cyclodextrin consisting of 6 D-glucopyranoside units, a β-cyclodextrin consisting of 7 D-glucopyranoside units, and a γ-cyclodextrin consisting of 8 D-glucopyranoside units). The physical and chemical properties of a parent cyclodextrin can be modified by derivatizing the hydroxyl groups with other functional groups.

In some embodiments, the pharmaceutical composition herein (e.g., any of those described in [1]-[37], [59], [60], [62] and [100]-[119] in the Brief Summary section herein, or any of AF1 to AF16, as applicable) can comprise a cyclodextrin derivative of the following formula:

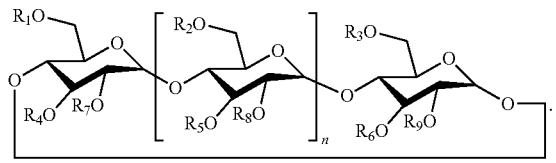

wherein: n is 4, 5, or 6;
wherein $R_1$, $R_2$, $R_3$, $R_4$, $R_5$, $R_6$, $R_7$, $R_8$, and $R_9$ are each, independently, —H, a straight chain or branched $C_1$-$C_8$-alkylene group, or an optionally substituted straight-chain or branched $C_1$-$C_6$ group, wherein at least one of $R_1$, $R_2$, $R_3$, $R_4$, $R_5$, $R_6$, $R_7$, $R_8$ and $R_9$ is a straight-chain or branched $C_1$-$C_8$-alkylene (e.g., $C_1$-$C_8$-(alkylene)-$SO_3^-$ group).

In some embodiments, the pharmaceutical composition herein (e.g., any of those described in [1]-[37], [59], [60], [62] and [100]-[119] in the Brief Summary section herein, or any of AF1 to AF16, as applicable) can comprise a cyclodextrin derivative of the following formula:

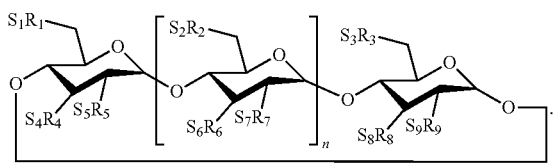

wherein: n is 4, 5, or 6;
wherein $R_1$, $R_2$, $R_3$, $R_4$, $R_5$, $R_6$, $R_7$, $R_8$, and $R_9$ are each, independently, —O— or a —O—(C2-C6 alkylene)-$SO_3^-$ group; wherein at least one of $R_1$ and $R_2$ is independently a —O—(C2-C6 alkylene)-$SO_3^-$ group; and 51, S2, S3, S4, S5, S6, S7, S8, and S9 are each, independently, a pharmaceutically acceptable cation. In further embodiments, the pharmaceutically acceptable cation is selected from: an alkali metal such as Li+, Na+, or K+; an alkaline earth metal such as $Ca^{+2}$, or $Mg^{+2}$ and ammonium ions and amine cations such as the cations of (C1-C6)-alkylamines, piperidine, pyrazine, (C1-C6)-alkanolamine and (C4-C8)-cycloalkanolamine. In some embodiments, at least one of R1 and R2 is independently a —O—(C2-C6 alkylene)-SO3- group that is a —O—$(CH_2)_m$SO3- group, wherein m is 2 to 6, preferably 2 to 4, (e.g., —O—CH2CH2CH2SO3$^-$ or —O—CH2CH2CH2CH2SO3$^-$); and $S_1$, $S_2$, $S_3$, $S_4$, $S_5$, $S_6$, $S_7$, $S_8$, and $S_9$ are each, independently, H or a pharmaceutically cation which includes for example, alkali metals (e.g., Li$^+$, Na$^+$, K$^+$) alkaline earth metals (e.g., $Ca^{+2}$, $Mg^{+2}$), ammonium ions and amine cations such as the cations of (C1-C6)-alkylamines, piperidine, pyrazine, ($C_1$-$C_6$)-alkanol-amine and ($C_4$-$C_8$)-cycloalkanolamine.

In some embodiments, the pharmaceutical composition herein (e.g., any of those described in [1]-[37], [59], [60], [62] and [100]-[119] in the Brief Summary section herein, or any of AF1 to AF16, as applicable) can comprise a cyclodextrin derivative of the following formula:

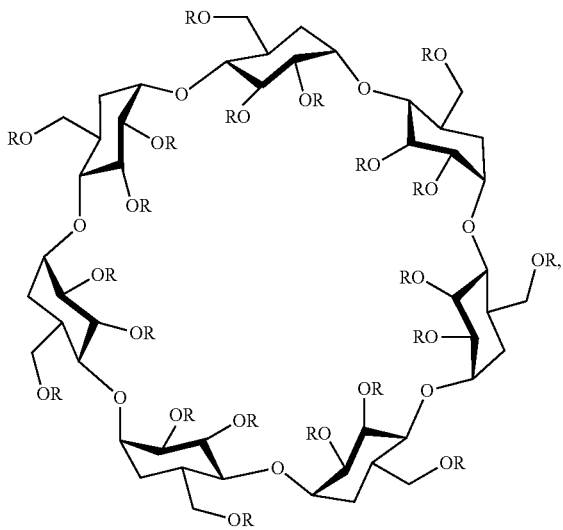

wherein R is:
  (a) $(H)_{21-x}$ or $(-(CH_2)_4-SO_3Na)_x$, and x=1.0-10.0, 1.0-5.0, 6.0-7.0, or 8.0-10.0;
  (b) $(H)_{21-x}$ or $(-(CH_2CH(OH)CH_3)_x$, and x=1.0-10.0, 1.0-5.0, 6.0-7.0, or 8.0-10.0;
  (c) $(H)_{21-x}$ or (sulfoalkyl ethers)$_x$, and x=1.0-10.0, 1.0-5.0, 6.0-7.0, or 8.0-10.0; or
  (d) $(H)_{21-x}$ or $(-(CH_2)_4-SO_3Na)_x$, and x=1.0-10.0, 1.0-5.0, 6.0-7.0, or 8.0-10.0.

In some embodiments, the pharmaceutical composition herein (e.g., any of those described in [1]-[37], [59], [60], [62] and [100]-[119] in the Brief Summary section herein, or any of AF1 to AF16, as applicable) can comprise a sulfoalkyl ether cyclodextrin, such as sulfoalkyl ether beta-cyclodextrin. In some embodiments, the pharmaceutical composition herein can comprise a hydroxyalkyl ether cyclodextrin, such as hydroxyalkyl ether beta-cyclodextrin. Non-limiting useful cyclodextrins for the pharmaceutical compositions herein can include any of those known in the art, such as those commercially available and any of those described in U.S. Pat. Nos. 6,133,248, 5,874,418, 6,046,177, 5,376,645, 5,134,127, 7,034,013, 6,869,939, 6,153,746, and 10,117,951; and Intl. Appl. Publ. No. WO 2005/117911, and WO 2009/134347, the content of each of which is herein incorporated by reference in its entirety.

For example, in some embodiments, the pharmaceutical composition herein (e.g., any of those described in [1]-[37], [59], [60], [62] and [100]-[119] in the Brief Summary section herein, or any of AF1 to AF16, as applicable) can comprise a sulfobutyl ether-β-cyclodextrin having an average degree of substitution of about 3-10, such as about 4.5-7.5 or about 6-7.1. One of such sulfobutyl ether beta-cyclodextrin is commercially available as CAPTISOL® (CyDex Pharmaceuticals, Inc., Lenexa, Kans.), which has the following chemical structure:

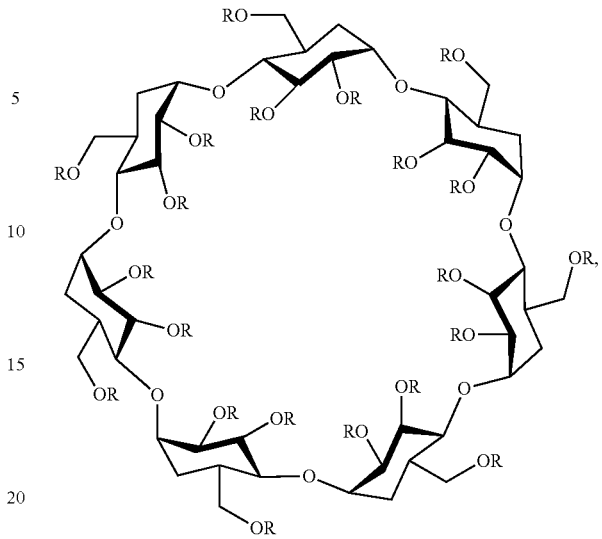

wherein R is $(-H)_{21-n}$ or $(CH2CH2CH2CH2SO3^-Na^+)_n$, and n is 6-7.1.

In some embodiments, the pharmaceutical composition herein can comprise a hydroxypropyl β-cyclodextrin, e.g., those having an average degree of substitution of about 1-10, such as about 2-8, such as about 4.2-6.3, such as about 4.5. Various hydroxypropyl β-cyclodextrins are also known in the art and commercially available, which can be used for the pharmaceutical compositions herein.

In some specific embodiments, the pharmaceutical composition can comprise (1) bortezomib; (2) mannitol; (3) hydroxypropyl β-cyclodextrin (HPβCD) (e.g., as described herein); and optionally (4) a water-soluble antioxidant (e.g., as described herein).

In some specific embodiments, the pharmaceutical composition can comprise (1) bortezomib; (2) mannitol; (3) sulfobutyl ether β-cyclodextrin (SBEβCD) (e.g., as described herein such as CAPTISOL®); and optionally (4) a water-soluble antioxidant (e.g., as described herein).

When present, the amount of water-soluble cyclodextrin in the pharmaceutical composition herein is typically in excess of the amount of bortezomib. In some preferred embodiments, the pharmaceutical composition herein (e.g., any of those described in [1]-[37], [59], [60], [62] and [100]-[119] in the Brief Summary section herein, or any of AF1 to AF16, as applicable) can comprise the water-soluble cyclodextrin (e.g., described herein, such as HPβCD or SBEβCD), wherein the pharmaceutical composition can be characterized by a weight ratio of the polyhydric alcohol to the water-soluble cyclodextrin ranging from about 1:10 to about 10:1, typically about 1:5 to about 5:1, e.g., e.g., about 1:3, about 1:1, about 2:1, about 5:1, or any ranges between the recited values. For example, in some embodiments, the pharmaceutical composition herein (e.g., any of those described in [1]-[37], [59], [60], [62] and [100]-[119] in the Brief Summary section herein, or any of AF1 to AF16, as applicable) can comprise mannitol and hydroxypropyl β-cyclodextrin (HPβCD), wherein the weight ratio of mannitol to hydroxypropyl β-cyclodextrin (HPβCD) can range from about 1:5 to about 5:1, e.g., about 5:1, about 4:1, about 3:1, about 2:1, about 1.5:1, about 1:1, about 1:1.5, about 1:2, about 1:3, about 1:4, about 1:5, or any ranges between the recited values. In some embodiments, the pharmaceutical composition herein (e.g., any of those described in [1]-[37],

[59], [60], [62] and [100]-[119] in the Brief Summary section herein, or any of AF1 to AF16, as applicable) can comprise mannitol and sulfobutyl ether β-cyclodextrin (SBEβCD), wherein the weight ratio of mannitol to sulfobutyl ether β-cyclodextrin (SBEβCD) can range from about 1:5 to about 5:1, e.g., about 5:1, about 4:1, about 3:1, about 2:1, about 1.5:1, about 1:1, about 1:1.5, about 1:2, about 1:3, about 1:4, about 1:5, or any ranges between the recited values such as about 2:1 to about 1:2. Without wishing to be bound by theories, it is believed that the use of a water-soluble cyclodextrin (e.g., described herein, such as HPβCD or SBEβCD) in the pharmaceutical compositions herein can provide additive or synergistic effect to that of the polyhydric alcohol (such as mannitol) in stabilizing bortezomib in an aqueous environment, which allows a stable aqueous bortezomib formulation to be prepared without using an organic solvent or without using an excessive amount of an organic solvent such as propylene glycol. Also, as shown in the Examples section, the use of a water-soluble cyclodextrin in the aqueous solution greatly suppressed the formation of an impurity with a relative retention time to bortezomib at 0.87. Aqueous formulations with the water-soluble cyclodextrin, after being stored at 40° C. for 3 months, were found to have undetectable amount of the impurity with a relative retention time to bortezomib at 0.87.

While the water-soluble cyclodextrin is typically used in combination with the polyhydric alcohol described herein, in some embodiments, the present disclosure also provides a pharmaceutical composition comprising bortezomib and the water-soluble cyclodextrin without the polyhydric alcohol. For example, in some embodiments, the present disclosure also provides a pharmaceutical composition comprising (1) bortezomib; (2) a water-soluble cyclodextrin; and optionally (3) a water-soluble antioxidant (e.g., as described herein), wherein the water-soluble cyclodextrin, and optional water-soluble antioxidant, and the amount/concentration thereof, include any of those described herein in any combinations. For example, the pharmaceutical composition can comprise (1) bortezomib; (2) hydroxypropyl β-cyclodextrin (HPβCD) (e.g., as described herein); and optionally (3) a water-soluble antioxidant (e.g., as described herein). In some specific embodiments, the pharmaceutical composition can comprise (1) bortezomib; (2) sulfobutyl ether β-cyclodextrin (SBEβCD) (e.g., as described herein such as CAPTISOL®); and optionally (3) a water-soluble antioxidant (e.g., as described herein).

In some embodiments, the pharmaceutical composition herein can also include a glycol and/or an alcohol. For example, in some embodiments, the pharmaceutical composition herein can comprise (1) bortezomib; (2) propylene glycol, benzyl alcohol, or a combination thereof. In some embodiments, the pharmaceutical composition can comprise the water-soluble cyclodextrin described herein and the propylene glycol, benzyl alcohol, or a combination thereof. However, in some embodiments, the pharmaceutical composition comprising the propylene glycol, benzyl alcohol, or a combination thereof can be free of the water-soluble cyclodextrin described herein. When present, the propylene glycol, benzyl alcohol, or combination thereof is typically present in a concentration of about 5 mg/mL to about 100 mg/mL, such as about 10 mg/mL to about 100 mg/mL, e.g., about 5 mg/mL, about 10 mg/mL, about 50 mg/mL, about 100 mg/mL, or any ranges between the recited values such as about 5-50 mg/mL or about 10-50 mg/mL.

In some embodiments, the pharmaceutical composition herein can comprise (1) bortezomib; (2) polyhydric alcohol; (3) propylene glycol, benzyl alcohol, or a combination thereof; and optionally (4) a water-soluble antioxidant, wherein the polyhydric alcohol, propylene glycol, benzyl alcohol, or a combination thereof, and optional water-soluble antioxidant, and the amount/concentration thereof, include any of those described herein in any combinations. For example, in some embodiments, the pharmaceutical composition can comprise (1) bortezomib; (2) mannitol; (3) propylene glycol, benzyl alcohol, or a combination thereof; and optionally (4) a water-soluble antioxidant (e.g., as described herein). In some embodiments, the pharmaceutical composition can comprise (1) bortezomib; (2) mannitol; (3) propylene glycol; and optionally (4) a water-soluble antioxidant (e.g., as described herein). In some embodiments, the pharmaceutical composition can comprise (1) bortezomib; (2) mannitol; (3) benzyl alcohol; and optionally (4) a water-soluble antioxidant (e.g., as described herein). In some embodiments, the pharmaceutical composition can comprise (1) bortezomib; (2) mannitol; (3) propylene glycol and benzyl alcohol; and optionally (4) a water-soluble antioxidant (e.g., as described herein). In some embodiments, the pharmaceutical composition in this paragraph can comprise a water-soluble cyclodextrin as described herein. However, in some embodiments, the pharmaceutical composition in this paragraph can also be free of a water-soluble cyclodextrin described herein.

While optional, a water-soluble antioxidant is typically included in the pharmaceutical composition herein. Antioxidants suitable for the pharmaceutical compositions herein are not particularly limited, which include any of those suitable for parental administration, such as those phenolic or sulfur containing antioxidants suitable for parenteral administration. In some embodiments, the water-soluble antioxidant in the pharmaceutical composition herein can comprise a sulfur containing antioxidant such as a sulfur containing amino acid, such as methionine, monothioglycerol, sodium metabisulfite. In some embodiments, the water-soluble antioxidant in the pharmaceutical composition herein can comprise methionine, monothioglycerol, sodium metabisulfite, butylated hydroxyanisole and/or butylated hydroxytoluene. In some embodiments, the water-soluble antioxidant in the pharmaceutical composition herein can also comprise other antioxidants that are pharmaceutically acceptable. For example, in some embodiments, the pharmaceutical composition herein can comprise (1) bortezomib; (2) polyhydric alcohol (e.g., described herein such as mannitol); (3) a sulfur containing amino acid, such as methionine; and optionally (4) a water-soluble cyclodextrin, wherein the polyhydric alcohol, sulfur containing amino acid, and optional water-soluble cyclodextrin, and the amount/concentration thereof, include any of those described herein in any combinations. For example, in some embodiments, the pharmaceutical composition herein can comprise (1) bortezomib; (2) mannitol; (3) a sulfur containing amino acid, such as methionine; and (4) a water-soluble cyclodextrin (e.g., described herein, such as HPβCD or SBEβCD).

In some embodiments, the pharmaceutical composition herein can comprise (1) bortezomib; (2) polyhydric alcohol (e.g., described herein such as mannitol); (3) monothioglycerol, sodium metabisulfite, butylated hydroxyanisole and/or butylated hydroxytoluene; and optionally (4) a water-soluble cyclodextrin, wherein the polyhydric alcohol and optional water-soluble cyclodextrin, and the amount/concentration thereof, include any of those described herein in any combinations. For example, in some embodiments, the pharmaceutical composition herein can comprise (1) bortezomib; (2) mannitol; (3) monothioglycerol, sodium metabisulfite, butylated hydroxyanisole and/or butylated hydroxytoluene; and (4) a water-soluble cyclodextrin (e.g., described herein, such as HPβCD or SBEβCD).

While the pharmaceutical composition herein typically includes the water-soluble antioxidant, in some embodiments, the pharmaceutical composition can also be free of the water-soluble antioxidant.

Typically, the pharmaceutical composition herein can comprise the water-soluble antioxidant in an amount effective to reduce oxidation of bortezomib. In some embodiments, the pharmaceutical composition herein (e.g., any of those described in [1]-[37], [59], [60], [62] and [100]-[119] in the Brief Summary section herein, or any of AF1 to AF16, as applicable) can comprise the water-soluble antioxidant in a concentration of about 0.1 mg/mL to about 10 mg/mL, such as about 0.5 mg/mL to about 10 mg/mL, e.g., about 0.5 mg/mL, about 1 mg/mL, about 2 mg/mL, about 5 mg/mL, about 10 mg/mL, or any ranges between the recited values. In some embodiments, the pharmaceutical composition herein (e.g., any of those described in [1]-[37], [59], [60], [62] and [100]-[119] in the Brief Summary section herein, or any of AF1 to AF16, as applicable) can comprise the water-soluble antioxidant in a concentration higher than 10 mg/mL, such as higher than 15 mg/mL, higher than 20 mg/mL, higher than 50 mg/mL, higher than 100 mg/mL, and up to the maximum solubility in the pharmaceutical composition.

In some embodiments, the pharmaceutical composition herein can also include optional other ingredients, such as a preservative, a chelating agent, an osmotic agent, a buffer, or a combination thereof.

For example, in some embodiments, the pharmaceutical composition herein can also include a chelating agent. Suitable chelating agents are not particularly limited so long as they are pharmaceutically acceptable, such as those suitable for parenteral administration. For example, in some embodiments, the chelating agent can be selected from the group consisting of: ethylene diamine tetraacetate (EDTA), methylglycinediacetic acid or N,N'-bis(carboxymethyl)alanine (MGDA), ethylene glycol tetraacetic acid (EGTA), (1,4,7,10-tetraazacyclododecane-1,4,7,10-tetraacetic acid) (DOTA), diethylene triamine penta acetic acid (DTPA), diethylene triamine penta methylene phosphonic acid (DTPMP), (1,4,10,13-tetraoxa-7,16-diazacyclooctadecane-7) (ODDA), (1,7,13-triaza-4,10,16-trioxacyclooctadecane-N,N',N"-triacetate) (TTTA), (tetraethyleneglycol-1,5,9-triazacyclododecane-N,N',N", tris(methylene phosphonic acid) (DOTRP), and mixtures thereof. In some specific embodiments, the chelating agent can be ethylene diamine tetraacetate (EDTA). In some embodiments, the pharmaceutical composition herein can also be free of a chelating agent as described herein. For example, in some embodiments, the pharmaceutical composition herein can be free of EDTA, MGDA, EGTA, DOTA, DTPA, DTPMP, ODDA, TTTA, DOTRP, and combinations thereof.

When present, the chelating agent such as EDTA is typically included in the pharmaceutical composition herein (e.g., any of those described in [1]-[37], [59], [60], [62] and [100]-[119] in the Brief Summary section herein, or any of AF1 to AF16, as applicable) at a concentration of about 0.01 mg/mL to about 10 mg/mL, such as about 0.01 mg/mL, about 0.1 mg/mL, about 0.5 mg/mL, about 1 mg/mL, about 2 mg/mL, about 5 mg/mL, about 10 mg/mL, or any ranges between the recited values. In some preferred embodiments, when present, the chelating agent (such as EDTA) can be included in the pharmaceutical composition herein (e.g., any of those described in [1]-[37], [59], [60], [62] and [100]-[119] in the Brief Summary section herein, or any of AF1 to AF16, as applicable) at a concentration of about 0.1 mg/mL to about 1 mg/mL.

In some embodiments, the pharmaceutical composition herein can also include a buffer. Buffers suitable for use in the pharmaceutical compositions herein are not particularly limited and include any of those known buffers suitable for use in a pharmaceutical composition, such as those suitable for use in a parenteral formulation. For example, in some embodiments, the buffer can be an acetate buffer, a phosphate based buffer, an amino acid based buffer, such as a glycine buffer, etc. In some embodiments, the buffer is a glycine buffer.

It was discovered that the pH of the pharmaceutical composition can have an impact on its stability. Typically, the pH of pharmaceutical composition herein is controlled between about 1.5 to about 5.0, such as about 1.5, about 2, about 3, about 3.5, about 4, about 4.5, about 5, or any ranges between the recited values. For example, in some embodiments, the pharmaceutical composition herein (e.g., any of those described in [1]-[37], [59], [60], [62] and [100]-[119] in the Brief Summary section herein, or any of AF1 to AF16, as applicable) can have a pH preferably between about 2 to about 4.5, such as about 3.5.

In any of the embodiments described herein, unless otherwise specified or contrary from context, the pharmaceutical composition herein can be characterized as being storage stable. For example, in any of the embodiments described herein, unless otherwise specified or contrary from context, the pharmaceutical composition herein (e.g., any of those described in [1]-[37], [59], [60], [62] and [100]-[119] in the Brief Summary section herein, or any of AF1 to AF16, as applicable), when stored at room temperature or at 40° C. for 1 month or longer, such as for 3 months or longer, the bortezomib composition has the bortezomib content maintained above 90% of the initial amount and the total degradation products formed about 10% or less. In any of the embodiments described herein, unless otherwise specified or contrary from context, the pharmaceutical composition herein (e.g., any of those described in [1]-[37], [59], [60], [62] and [100]-[119] in the Brief Summary section herein, or any of AF1 to AF16, as applicable), when stored at room temperature or 40° C. for 1 month or longer, such as for 3 months or longer, can have any one or more of the following characteristics: (1) the pharmaceutical composition has the bortezomib content maintained above 90% of the initial amount; (2) the total degradation products formed in the pharmaceutical composition are about 10% or less; (3) each of the degradation impurities A, D, C1, and C2 in the pharmaceutical composition is in an amount of about 8% or less; (4) the degradation impurity A in the pharmaceutical composition is in an amount of about 8% or less, such as about 7% or less, about 6% or less, about 5% or less, about 4% or less, about 3% or less, about 2% or less, or about 1% or less; (5) the degradation impurity D in the pharmaceutical composition is in an amount of about 6% or less, such as about 5% or less, about 4% or less, about 3% or less, about 2% or less, or about 1% or less; (6) the degradation impurity C1 in the pharmaceutical composition is in an amount of about 5% or less, such as about 4% or less, about 3% or less, about 2% or less, or about 1% or less; (7) the degradation impurity C2 in the pharmaceutical composition is in an amount of about 5% or less, such as about 4% or less, about 3% or less, about 2% or less, or about 1% or less; and (8) the impurity with a relative retention time of about 0.87-0.88 (see e.g., FIG. 1) is in an amount of about 1% or less, 0.5% or less, 0.1% or less, or in a non-detectable amount. For example, in some embodiments, the pharmaceutical composition herein (e.g., any of those described in [1]-[37], [59], [60], [62] and [100]-[119] in the Brief Summary section herein, or any of AF1 to AF16, as applicable), when stored at 40° C. for 1 month or longer, such as for 3 months or longer, can have each of the characteristics (1)-(8), or any combinations thereof, such as (1)-(2), (1)-(3), (1)-(4), (1)-(5), (1)-(6), (1)-(7), (1)-(8), (1), (2), and (4), etc. In some embodiments, the pharmaceutical composition herein (e.g., any of those described in [1]-[37], [59], [60], [62] and [100]-[119] in the Brief Summary section herein, or any of AF1 to AF16, as applicable), when stored at room temperature for 1 month or longer, such as for 3 months or longer, can have any of the characteristics (1)-(8), or any combinations thereof, such as (1)-(2), (1)-(3), (1)-(4), (1)-(5), (1)-(6), (1)-(7), (1)-(8), (1), (2), and (4), etc. The identities of degradation impurities A, D, C1, and C2, as well as exemplary analytical methods for measuring the levels of these degradation impurities, are disclosed in the Examples section herein.

In some embodiments, the present disclosure provides a long-term (e.g., 1 month or longer, such as 3 months or longer) storage stable aqueous compositions of bortezomib or its pharmaceutically acceptable salt form comprising:

1) bortezomib or its pharmaceutically acceptable salt form, wherein the concentration bortezomib is about 0.5 mg/mL to about 3.5 mg/mL, exemplary concentrations also include those described herein,
2) at least one or more pharmaceutically acceptable polyhydroxy excipients, wherein the weight ratio of bortezomib to the polyhydroxy excipients is about 1:10 to about 1:200, exemplary ratios also include those described herein,
3) a pharmaceutically acceptable antioxidant, preferably a sulfur containing antioxidant, exemplary antioxidants also include those described herein,
4) an aqueous solution with a pH range of about 1.5 to about 5.0, wherein the solution is essentially free of organic solvents
5) one or more optional pharmaceutical additives, such as osmotic agents, chelating agents, and antimicrobial preservatives, etc.

Exemplary Pharmaceutical Compositions Comprising Bortezomib

In some embodiments, the present disclosure also provides the following non-limiting exemplary pharmaceutical compositions AF1-AF16.

Aqueous Formulation 1 ("AF1"). Aqueous Formulation 1 comprises (1) bortezomib; (2) a polyhydric alcohol (e.g., described herein); and (3) a water-soluble antioxidant (e.g., described herein) in water, wherein bortezomib is in a concentration ranging from about 0.5 mg/mL to about 3.5 mg/mL, e.g., about 1 mg/mL, about 1.5 mg/mL, about 2 mg/mL, about 2.5 mg/mL, about 3 mg/mL or about 3.5 mg/mL, or any ranges between the recited values, wherein the polyhydric alcohol is in an amount of about 50 mg/mL to about 300 mg/mL, such as about 60 mg/mL, about 80 mg/mL, about 100 mg/mL, about 125 mg/mL, about 150 mg/mL, about 200 mg/mL, about 250 mg/mL, or about 300 mg/mL, or any ranges between the recited values, wherein the water-soluble antioxidant is in an amount of about 0.1 mg/mL to about 5 mg/mL, e.g., about 1 mg/mL, about 2 mg/mL, about 3 mg/mL, about 4 mg/mL, about 5 mg/mL, or any ranges between the recited values, and wherein water is in an amount of greater than 50% by weight, e.g., about 60%, about 70%, about 80%, about 85%, about 90%, about 95%, or any ranges between the recited values, such as about 60-85%, about 60-95%, about 70-80%, about 70-90%, etc. In some embodiments according to AF1, the polyhydric alcohol comprises mannitol. In some embodiments according to AF1, the water-soluble antioxidant comprises a sulfur containing antioxidant, such as a sulfur containing amino acid, such as methionine. In some embodiments according to AF1, the water-soluble antioxidant comprises a sulfur containing antioxidant, such as monothioglycerol and/or sodium metabisulfite. In some embodiments according to AF1, the formulation can further include optional ingredients. In some embodiments according to AF1, the formulation comprises (1) bortezomib; (2) mannitol; and (3) methionine. In some embodiments according to AF1, the formulation comprises (1) bortezomib; (2) mannitol; (3) methionine; and (4) an optional chelating agent (e.g., EDTA). In some embodiments according to AF1, the formulation comprises (1) bortezomib; (2) mannitol; (3) methionine; and (4) an optional buffer (e.g., glycine). In some embodiments according to AF1, the formulation comprises (1) bortezomib; (2) mannitol; (3) methionine; and (4) EDTA. In some embodiments according to AF1, the formulation comprises (1) bortezomib; (2) mannitol; (3) methionine; and (4) glycine. In some embodiments according to AF1, the formulation comprises (1) bortezomib; (2) mannitol; (3) methionine; (4) EDTA and (5) glycine. Suitable optional ingredients as well as the respective amounts include any of those described herein in any combinations.

Aqueous Formulation 2 ("AF2"). Aqueous Formulation 2 comprises (1) bortezomib; (2) a polyhydric alcohol (e.g., described herein); (3) a water-soluble cyclodextrin (e.g., described herein); and (4) a water-soluble antioxidant (e.g., as described herein) in water, wherein bortezomib is in a concentration ranging from about 0.5 mg/mL to about 3.5 mg/mL, e.g., about 1 mg/mL, about 1.5 mg/mL, about 2 mg/mL, about 2.5 mg/mL, about 3 mg/mL or about 3.5 mg/mL, or any ranges between the recited values, wherein the polyhydric alcohol is in an amount of about 50 mg/mL to about 300 mg/mL, such as about 60 mg/mL, about 80 mg/mL, about 100 mg/mL, about 125 mg/mL, about 150 mg/mL, about 200 mg/mL, about 250 mg/mL, or about 300 mg/mL, or any ranges between the recited values, wherein the water-soluble cyclodextrin is in an amount of about 50 mg/mL to about 300 mg/mL, such as about 60 mg/mL, about 80 mg/mL, about 100 mg/mL, about 125 mg/mL, about 150 mg/mL, about 200 mg/mL, about 250 mg/mL, or about 300 mg/mL, or any ranges between the recited values, wherein the water-soluble antioxidant is in an amount of about 0.5 mg/mL to about 5 mg/mL, e.g., about 1 mg/mL, about 2 mg/mL, about 3 mg/mL, about 4 mg/mL, about 5 mg/mL, or any ranges between the recited values, and wherein water is in an amount of greater than 50% by weight, e.g., about 60%, about 70%, about 80%, about 85%, about 90%, about 95%, or any ranges between the recited values, such as about 60-85%, about 60-95%, about 70-80%, about 70-90%, etc. In some embodiments according to AF2, the polyhydric alcohol comprises mannitol. In some embodiments according to AF2, the water-soluble cyclodextrin comprises a hydroxypropyl beta-cyclodextrin described herein. In some embodiments according to AF2, the water-soluble cyclodextrin comprises a sulfobutyl ether beta-cyclodextrin described herein. In some embodiments according to AF2, the water-soluble antioxidant comprises a sulfur containing antioxidant, such as a sulfur containing amino acid, such as methionine. In some embodiments according to AF2, the water-soluble antioxidant comprises a sulfur containing antioxidant, such as monothioglycerol and/or sodium metabisulfite. In some embodiments according to AF2, the formulation is free of propylene glycol. In some embodiments according to AF2, the formulation is free of benzyl alcohol. In some embodiments according to AF2, the formulation is free of propylene glycol and benzyl alcohol. In some embodiments according to AF2, the formulation can further include optional ingredients. Suitable optional ingredients as well as the respective amounts include any of those described herein in any combinations.

Aqueous Formulation 3 ("AF3"). Aqueous Formulation 3 comprises (1) bortezomib; (2) polyhydric alcohol (e.g., described herein); (3) propylene glycol, benzyl alcohol, or a combination thereof; and (4) a water-soluble antioxidant (e.g., as described herein) in water, wherein bortezomib is in a concentration ranging from about 0.5 mg/mL to about 3.5 mg/mL, e.g., about 1 mg/mL, about 1.5 mg/mL, about 2 mg/mL, about 2.5 mg/mL, about 3 mg/mL or about 3.5 mg/mL, or any ranges between the recited values, wherein the polyhydric alcohol is in an amount of about 50 mg/mL to about 300 mg/mL, such as about 60 mg/mL, about 80 mg/mL, about 100 mg/mL, about 125 mg/mL, about 150 mg/mL, about 200 mg/mL, about 250 mg/mL, or about 300 mg/mL, or any ranges between the recited values, wherein the propylene glycol, benzyl alcohol, or combination thereof is present in a concentration of about 5 mg/mL to about 100 mg/mL, such as about 10 mg/mL to about 100 mg/mL, e.g., about 5 mg/mL, about 10 mg/mL, about 50 mg/mL, about 100 mg/mL, or any ranges between the recited values such as about 5-50 mg/mL or about 10-50 mg/mL, wherein the water-soluble antioxidant is in an amount of about 0.5 mg/mL to about 5 mg/mL, e.g., about 1 mg/mL, about 2 mg/mL, about 3 mg/mL, about 4 mg/mL, about 5 mg/mL, or any ranges between the recited values, and wherein water is in an amount of greater than 50% by weight, e.g., about 60%, about 70%, about 80%, about 85%, about 90%, about 95%, or any ranges between the recited values, such as about 60-85%, about 60-95%, about 70-80%, about 70-90%, etc. In some embodiments according to AF3, the polyhydric alcohol comprises mannitol. In some embodiments according to AF3, the formulation comprises propylene glycol. In some embodiments according to AF3, the formulation comprises benzyl alcohol. In some embodiments according to AF3, the formulation comprises both propylene glycol and benzyl alcohol. In some embodiments according to AF3, the water-soluble antioxidant comprises a sulfur containing antioxidant, such as a sulfur containing amino acid, such as methionine. In some embodiments according to AF3, the water-soluble antioxidant comprises a sulfur containing antioxidant, such as monothioglycerol and/or sodium metabisulfite. In some embodiments according to AF3, the formulation is free of a water-soluble cyclodextrin. In some embodiments according to AF3, the formulation can further include optional ingredients. In some embodiments according to AF3, the formulation further comprises a buffer, such as a glycine buffer. Suitable optional ingredients as well as the respective amounts include any of those described herein in any combinations.

Aqueous Formulation 4 ("AF4"). Aqueous Formulation 4 comprises (1) bortezomib and (2) polyhydric alcohol (e.g., as described herein) in water, wherein bortezomib is in a concentration ranging from about 0.5 mg/mL to about 3.5 mg/mL, e.g., about 1 mg/mL, about 1.5 mg/mL, about 2 mg/mL, about 2.5 mg/mL, about 3 mg/mL or about 3.5 mg/mL, or any ranges between the recited values, wherein the polyhydric alcohol is in an amount of about 50 mg/mL to about 300 mg/mL, such as about 60 mg/mL, about 80 mg/mL, about 100 mg/mL, about 125 mg/mL, about 150 mg/mL, about 200 mg/mL, about 250 mg/mL, or about 300 mg/mL, or any ranges between the recited values, and wherein water is in an amount of greater than 50% by weight, e.g., about 60%, about 70%, about 80%, about 85%, about 90%, about 95%, or any ranges between the recited values, such as about 60-85%, about 60-95%, about 70-80%, about 70-90%, etc. In some embodiments according to AF4, the polyhydric alcohol comprises mannitol. In some embodiments according to AF4, the formulation can further include optional ingredients. Suitable optional ingredients as well as the respective amounts include any of those described herein in any combinations.

Aqueous Formulation 5 ("AF5"). Aqueous Formulation 5 comprises (1) bortezomib; (2) a polyhydric alcohol (e.g., as described herein); and (3) a water-soluble cyclodextrin (e.g., as described herein) in water, wherein bortezomib is in a concentration ranging from about 0.5 mg/mL to about 3.5 mg/mL, e.g., about 1 mg/mL, about 1.5 mg/mL, about 2 mg/mL, about 2.5 mg/mL, about 3 mg/mL or about 3.5 mg/mL, or any ranges between the recited values, wherein the polyhydric alcohol is in an amount of about 50 mg/mL to about 300 mg/mL, such as about 60 mg/mL, about 80 mg/mL, about 100 mg/mL, about 125 mg/mL, about 150 mg/mL, about 200 mg/mL, about 250 mg/mL, or about 300 mg/mL, or any ranges between the recited values, wherein the water-soluble cyclodextrin is in an amount of about 50 mg/mL to about 300 mg/mL, such as about 60 mg/mL, about 80 mg/mL, about 100 mg/mL, about 125 mg/mL, about 150 mg/mL, about 200 mg/mL, about 250 mg/mL, or about 300 mg/mL, or any ranges between the recited values, and wherein water is in an amount of greater than 50% by weight, e.g., about 60%, about 70%, about 80%, about 85%, about 90%, about 95%, or any ranges between the recited values, such as about 60-85%, about 60-95%, about 70-80%, about 70-90%, etc. In some embodiments according to AF5, the polyhydric alcohol comprises mannitol. In some embodiments according to AF5, the water-soluble cyclodextrin comprises a hydroxypropyl beta-cyclodextrin described herein. In some embodiments according to AF5, the water-soluble cyclodextrin comprises a sulfobutyl ether beta-cyclodextrin described herein. In some embodiments according to AF5, the formulation is free of propylene glycol. In some embodiments according to AF5, the formulation is free of benzyl alcohol. In some embodiments according to AF5, the formulation is free of propylene glycol and benzyl alcohol. In some embodiments according to AF5, the formulation can further include optional ingredients. Suitable optional ingredients as well as the respective amounts include any of those described herein in any combinations.

Aqueous Formulation 6 ("AF6"). Aqueous Formulation 6 comprises (1) bortezomib; (2) polyhydric alcohol (e.g., as described herein); and (3) propylene glycol, benzyl alcohol, or a combination thereof, in water, wherein bortezomib is in a concentration ranging from about 0.5 mg/mL to about 3.5 mg/mL, e.g., about 1 mg/mL, about 1.5 mg/mL, about 2 mg/mL, about 2.5 mg/mL, about 3 mg/mL or about 3.5 mg/mL, or any ranges between the recited values, wherein the polyhydric alcohol is in an amount of about 50 mg/mL to about 300 mg/mL, such as about 60 mg/mL, about 80 mg/mL, about 100 mg/mL, about 125 mg/mL, about 150 mg/mL, about 200 mg/mL, about 250 mg/mL, or about 300 mg/mL, or any ranges between the recited values, wherein the propylene glycol, benzyl alcohol, or combination thereof is present in a concentration of about 5 mg/mL to about 100 mg/mL, such as about 10 mg/mL to about 100 mg/mL, e.g., about 5 mg/mL, about 10 mg/mL, about 50 mg/mL, about 100 mg/mL, or any ranges between the recited values such as about 5-50 mg/mL or about 10-50 mg/mL, and wherein water is in an amount of greater than 50% by weight, e.g., about 60%, about 70%, about 80%, about 85%, about 90%, about 95%, or any ranges between the recited values, such as about 60-85%, about 60-95%, about 70-80%, about 70-90%, etc. In some embodiments according to AF6, the polyhydric alcohol comprises mannitol. In some embodiments according to AF6, the formulation comprises propylene glycol. In some embodiments according to AF6, the formulation comprises benzyl alcohol. In some embodiments according to AF6, the formulation comprises both propylene glycol and benzyl alcohol. In some embodiments according to AF3, the formulation is free of a water-soluble cyclodextrin. In some embodiments according to AF6, the formulation can further include optional ingredients. Suitable optional ingredients as well as the respective amounts include any of those described herein in any combinations.

Aqueous Formulation 7 ("AF7"). Aqueous Formulation 7 comprises (1) bortezomib; (2) polyhydric alcohol (e.g., as described herein); (3) a water-soluble cyclodextrin (e.g., as described herein); (4) propylene glycol, benzyl alcohol, or a combination thereof; and (5) optionally a water-soluble antioxidant (e.g., as described herein) in water, wherein bortezomib is in a concentration ranging from about 0.5 mg/mL to about 3.5 mg/mL, e.g., about 1 mg/mL, about 1.5 mg/mL, about 2 mg/mL, about 2.5 mg/mL, about 3 mg/mL or about 3.5 mg/mL, or any ranges between the recited values, wherein the polyhydric alcohol is in an amount of about 50 mg/mL to about 300 mg/mL, such as about 60 mg/mL, about 80 mg/mL, about 100 mg/mL, about 125 mg/mL, about 150 mg/mL, about 200 mg/mL, about 250 mg/mL, or about 300 mg/mL, or any ranges between the recited values, wherein the water-soluble cyclodextrin is in an amount of about 50 mg/mL to about 300 mg/mL, such as about 60 mg/mL, about 80 mg/mL, about 100 mg/mL, about 125 mg/mL, about 150 mg/mL, about 200 mg/mL, about 250 mg/mL, or about 300 mg/mL, or any ranges between the recited values, wherein the propylene glycol, benzyl alcohol, or combination thereof is present in a concentration of about 5 mg/mL to about 100 mg/mL, such as about 10 mg/mL to about 100 mg/mL, e.g., about 5 mg/mL, about 10 mg/mL, about 50 mg/mL, about 100 mg/mL, or any ranges between the recited values such as about 5-50 mg/mL or about 10-50 mg/mL, wherein the water-soluble antioxidant, if present, is in an amount of about 0.5 mg/mL to about 5 mg/mL, e.g., about 1 mg/mL, about 2 mg/mL, about 3 mg/mL, about 4 mg/mL, about 5 mg/mL, or any ranges between the recited values, and wherein water is in an amount of greater than 50% by weight, e.g., about 60%, about 70%, about 80%, about 85%, about 90%, about 95%, or any ranges between the recited values, such as about 60-85%, about 60-95%, about 70-80%, about 70-90%, etc. In some embodiments according to AF7, the polyhydric alcohol comprises mannitol. In some embodiments according to AF7, the water-soluble cyclodextrin comprises a sulfobutyl ether beta-cyclodextrin described herein. In some embodiments according to AF7, the formulation comprises propylene glycol. In some embodiments according to AF7, the formulation comprises benzyl alcohol. In some embodiments according to AF7, the formulation comprises both propylene glycol and benzyl alcohol. In some embodiments according to AF7, the formulation does not include the optional water-soluble antioxidant. In some embodiments according to AF7, the formulation comprises the water-soluble antioxidant. For example, in some embodiments according to AF7, the formulation comprises a sulfur containing antioxidant, such as a sulfur containing amino acid, such as methionine. In some embodiments according to AF7, the formulation comprises a sulfur containing antioxidant, such as monothioglycerol and/or sodium metabisulfite. In some embodiments according to AF7, the formulation can further include optional ingredients. Suitable optional ingredients as well as the respective amounts include any of those described herein in any combinations.

Aqueous Formulation 8 ("AF8"). Aqueous Formulation 8 can have the composition of any one of AF1-AF7, further characterized in that it is free of a chelating agent described herein. For example, in some embodiments, AF8 can be free of EDTA, MGDA, EGTA, DOTA, DTPA, DTPMP, ODDA, TTTA, DOTRP, and combinations thereof.

Aqueous Formulation 9 ("AF9"). Aqueous Formulation 9 can have the composition of any one of AF1-AF7, further characterized in that it comprises a chelating agent described herein. For example, in some embodiments, AF9 can comprise EDTA at a concentration of about 0.01 mg/mL to about 10 mg/mL, such as about 0.01 mg/mL, about 0.1 mg/mL, about 0.5 mg/mL, about 1 mg/mL, about 2 mg/mL, about 5 mg/mL, about 10 mg/mL, or any ranges between the recited values such as about 0.1-1 mg/mL.

Aqueous Formulation 10 ("AF10"). Aqueous Formulation 10 can have the composition of any one of AF1-AF9, further characterized in that it has a pH of about 1.5 to about 5.0, such as about 1.5, about 2, about 3, about 3.5, about 4, about 4.5, about 5, or any ranges between the recited values, such as about 2 to about 4.5, such as about 3.5.

Aqueous Formulation 11 ("AF11"). Aqueous Formulation 11 can have the composition of any one of AF1-AF10, further characterized in that (1) the weight ratio of bortezomib to the polyhydric alcohol (e.g., mannitol) ranges from about 1:10 to about 1:200, e.g., about 1:20, about 1:50, about 1:100, about 1:150, or about 1:200, or any ranges between the recited values; (2) as applicable, the weight ratio of the polyhydric alcohol (e.g., mannitol) to the water-soluble cyclodextrin (e.g., sulfobutyl ether beta-cyclodextrin) ranges from about 1:5 to about 5:1, e.g., about 1:3, about 1:1, about 2:1, about 5:1, or any ranges between the recited values; or (3) as applicable, a combination of (1) and (2).

Aqueous Formulation 12 ("AF12"). Aqueous Formulation 12 comprises (1) bortezomib; (2) mannitol; and (3) sulfobutyl ether beta-cyclodextrin in water, and can have the composition and characteristics described in any of the aqueous solution in [24]-[37] of the Brief Summary section. In some embodiments according to AF12, the formulation is free of propylene glycol. In some embodiments according to AF12, the formulation is free of benzyl alcohol. In some embodiments according to AF12, the formulation is free of propylene glycol and benzyl alcohol. In some embodiments according to AF12, the formulation can further include optional ingredients. Suitable optional ingredients as well as the respective amounts include any of those described herein in any combinations.

Aqueous Formulation 13 ("AF13"). Aqueous Formulation 13 can have the composition of AF12, further characterized in that (1) the mannitol is in an amount of about 50 mg/mL to about 300 mg/mL, such as about 60 mg/mL, about 80 mg/mL, about 100 mg/mL, about 125 mg/mL, about 150 mg/mL, about 200 mg/mL, about 250 mg/mL, or about 300 mg/mL, or any ranges between the recited values, and/or (2) the sulfobutyl ether beta-cyclodextrin is in an amount of about 50 mg/mL to about 300 mg/mL, such as about 60 mg/mL, about 80 mg/mL, about 100 mg/mL, about 125 mg/mL, about 150 mg/mL, about 200 mg/mL, about 250 mg/mL, or about 300 mg/mL, or any ranges between the recited values.

Aqueous Formulation 14 ("AF14"). Aqueous Formulation 14 can have the composition of AF12 or AF13, further characterized in that the formulation is free of a chelating agent described herein. For example, in some embodiments, AF14 can be free of EDTA, MGDA, EGTA, DOTA, DTPA, DTPMP, ODDA, TTTA, DOTRP, and combinations thereof.

Aqueous Formulation 15 ("AF15"). Aqueous Formulation 15 can have the composition of AF12 or AF13, further characterized in that the formulation comprises a chelating agent described herein. For example, in some embodiments, AF15 can comprise EDTA at a concentration of about 0.01 mg/mL to about 10 mg/mL, such as about 0.01 mg/mL, about 0.1 mg/mL, about 0.5 mg/mL, about 1 mg/mL, about 2 mg/mL, about 5 mg/mL, about 10 mg/mL, or any ranges between the recited values such as about 0.1-1 mg/mL.

Aqueous Formulation 16 ("AF16"). Aqueous Formulation 16 can have the composition of any one of AF1 to AF15, further characterized in that the bortezomib is at a concentration of about 1 mg/mL to about 3.5 mg/mL, e.g., about 1 mg/mL, about 2.5 mg/mL.

In any of the embodiments described herein according to AF1 to AF16, unless otherwise specified or contrary from context, the aqueous formulation can be essentially free or substantially free of dissolved oxygen.

In any of the embodiments described herein according to AF1 to AF16, unless otherwise specified or contrary from context, the aqueous formulation can be storage stable (e.g., described herein).

In any of the embodiments described herein according to AF1 to AF16, unless otherwise specified or contrary from context, the aqueous formulation is suitable for pharmaceutical use, such as suitable for parenteral injection, in particular, intravenous or subcutaneous injection.

In any of the embodiments described herein according to AF1 to AF16, unless otherwise specified or contrary from context, the aqueous formulation can be an aqueous solution suitable for pharmaceutical use, such as suitable for parenteral injection, in particular, intravenous or subcutaneous injection.

In any of the embodiments described herein according to AF1 to AF16, unless otherwise specified or contrary from context, the aqueous formulation can be a ready-to-use formulation, which can be used directly without further handling, such as reconstitution and/or dilution.

In any of the embodiments described herein according to AF1 to AF16, unless otherwise specified or contrary from context, the aqueous formulation can be in a single-dose dosage form, such as packaged in an ampoule, a vial, a cartridge, a pre-filled syringe, or an intravenous bag.

In any of the embodiments described herein according to AF1 to AF16, unless otherwise specified or contrary from context, the aqueous formulation can be in a multi-dose dosage form.

Methods of Preparing Pharmaceutical Compositions Comprising Bortezomib

In some embodiments, the present disclosure also provides a method of preparing the pharmaceutical compositions herein.

In a broad aspect, the methods of preparing the pharmaceutical compositions herein typically include mixing the ingredients in the desired amount/concentration described herein in water. For example, in some embodiments, the ingredients and the respective amount in the pharmaceutical composition can be any of those described in [1]-[37], [59], [60], [62] and [100]-[119] in the Brief Summary section herein, as applicable, or any of those described in AF1-AF16.

In some particular embodiments, the method of preparation herein comprises mixing in water (1) bortezomib with (2) a polyhydric alcohol; and optionally (3) a water-soluble antioxidant, and optional other ingredients, to form the pharmaceutical composition, wherein the polyhydric alcohol, optional water-soluble antioxidant, and optional other ingredients, as well as the respective amount/concentration thereof, include any of those described herein in any combinations. In some embodiments, the mixing can comprise a) dissolving the polyhydric alcohol and optional water-soluble antioxidant, and optional other ingredients, in water to form an aqueous excipient mixture; and b) adding bortezomib to the aqueous excipient mixture to form the pharmaceutical composition. In some embodiments, the method can further comprise adjusting the pH of the pharmaceutical composition to about 1.5 to about 5.0, such as about 1.5, about 2, about 3, about 3.5, about 4, about 4.5, about 5, or any ranges between the recited values.

In some embodiments, the method of preparation herein can include a sterilization step.

Typically, during the preparation of the pharmaceutical compositions herein, one or more steps of removing oxygen in the pharmaceutical compositions or an intermediate composition can be carried out. For example, in some embodiments, the aqueous excipient mixture can be deoxygenated to reduce or remove the dissolved oxygen. In some embodiments, the water used for the preparation can be deoxygenated to reduce or remove the dissolved oxygen. In some embodiments, deoxygenating can comprise sparging an inert gas such as N2 or Ar to the water or the aqueous excipient mixture or the pharmaceutical composition.

In some embodiments, the method of preparation herein can further include packaging or sealing the pharmaceutical composition in a suitable container, such as an ampoule, a vial, a cartridge, a pre-filled syringe, or an intravenous bag. In some embodiments, prior to sealing the suitable container, inert gas such as N2 or Ar can be used to replace the air in the container or otherwise reduce the oxygen content in the headspace of the container.

In some embodiments, the method of preparation herein is for preparing a single-dose dosage form.

In some embodiments, the method of preparation herein is for preparing a multi-dose dosage form.

In any of the embodiments according to the method of preparation herein, unless otherwise specified or contrary from context, the method is for preparing a ready-to-use formulation, which does not include lyophilizing the pharmaceutical composition herein comprising the (1) bortezomib; (2) polyhydric alcohol; (3) optional water-soluble antioxidant, and optional other ingredients in water.

However, in some embodiments, the method can also comprise lyophilizing the pharmaceutical composition comprising the (1) bortezomib; (2) polyhydric alcohol; (3) optional water-soluble antioxidant, and optional other ingredients in water to form a lyophilized powder, which can be reconstituted prior to use.

In some embodiments, the bortezomib used for the method of preparation herein (e.g., any of the methods described in [39]-[61]) can be a solid state bortezomib, such as a lyophilized bortezomib, such as those derived from lyophilizing bortezomib with a stabilizer, including but not limited to mannitol, boric acid, tromethamine, etc. In some embodiments, the solid state bortezomib can be a crystalline form of bortezomib, which includes any of those polymorphic forms known in the art. In some embodiments, the solid state bortezomib can be an ester form of bortezomib, such as a mannitol ester of bortezomib.

In some embodiments, the bortezomib used for the method of preparation herein (e.g., any of the methods described in [39]-[61]) can be first dissolved in a solvent, such as propylene glycol, ethanol, benzyl alcohol, etc., typically in a small volume, before the bortezomib is mixed with other ingredients, such as before it is added into the aqueous excipient mixture herein. However, in some embodiments, bortezomib in a solid state can be used directly for the method of preparation herein.

In some particular embodiments, the pharmaceutical composition herein can also be prepared by mixing the aqueous excipient mixture having the ingredients described herein with a solid state bortezomib, such as a lyophilized bortezomib, such as those derived from lyophilizing bortezomib with a stabilizer, including but not limited to mannitol, boric acid, tromethamine, etc. For example, in some embodiments, the aqueous excipient mixture can be prepared by a method of dissolving the polyhydric alcohol and optional water-soluble antioxidant, and optional other ingredients, in water. In some embodiments, the aqueous excipient mixture can be adjusted to have a pH of about 1.5 to about 5.0, such as about 1.5, about 2, about 3, about 3.5, about 4, about 4.5, about 5, or any ranges between the recited values. In some embodiments, the method of preparing the aqueous excipient mixture can include a step of sterilizing the aqueous excipient mixture. Typically, the aqueous excipient mixture can be deoxygenated to reduce or remove the dissolved oxygen. In some embodiments, deoxygenating can comprise sparging an inert gas such as N2 or Ar to the water or the aqueous excipient mixture. Typically, in such embodiments, a kit comprising the aqueous excipient mixture and the solid state bortezomib can be provided. The ingredients and the respective amount in the aqueous excipient mixture can include any of those described herein, for example, as described in [1]-[37], [59], [60], [62] and [100]-[119] in the Brief Summary section herein, as applicable, or any of those described in AF1-AF16, without the bortezomib.

In some more specific embodiments, the present disclosure provides a method of preparing an aqueous solution according to AF12 ("AS12") suitable for pharmaceutical use (e.g., parenteral injection, such as intravenous or subcutaneous injection), the method comprising mixing bortezomib with mannitol, sulfobutyl ether beta-cyclodextrin, an optional water-soluble antioxidant, and optional other ingredients, in water to form the aqueous solution. In some embodiments, AS12 comprises the optional water-soluble antioxidant, e.g., as described herein. In some embodiments, AS12 comprises one or more optional other ingredients. In some embodiments, the optional other ingredients comprise propylene glycol, benzyl alcohol, a preservative, a chelating agent, an osmotic agent, a buffer, or a combination thereof. The ingredients and the respective amount for AS12 can include any of those described herein for AF12-AF16, as applicable or those shown in [44]-[58] in the Brief Summary section herein.

In some embodiments, the mixing in the method of preparing AS12 can comprise: (a) Dissolving the mannitol, sulfobutyl-ether beta-cyclodextrin, optional water-soluble antioxidant, and optional other ingredients in water to form an aqueous excipient mixture; and (b) Adding bortezomib to the aqueous excipient mixture to form the aqueous solution. In some embodiments, the method further comprises sterilizing the aqueous solution. In some embodiments, the method further comprises adjusting the pH of the aqueous solution to about 1.5 to about 5.0, such as about 1.5, about 2, about 3, about 3.5, about 4, about 4.5, about 5, or any ranges between the recited values.

In some embodiments, the method of preparing AS12 further comprises one or more steps of removing oxygen in the aqueous solution or an intermediate composition. For example, in some embodiments, the water used for the preparation, the aqueous excipient mixture, and/or the aqueous solution can be deoxygenated to reduce or remove the dissolved oxygen. In some embodiments, deoxygenating can comprise sparging an inert gas such as N2 or Ar to the water or the aqueous excipient mixture or the aqueous solution.

In some embodiments, the method of preparing AS12 can further include packaging or sealing the aqueous solution in a suitable container, such as an ampoule, a vial, a cartridge, a pre-filled syringe, or an intravenous bag. In some embodiments, prior to sealing the suitable container, inert gas such as N2 or Ar can be used to replace the air in the container or otherwise reduce the oxygen content in the headspace of the container.

In some embodiments, the aqueous solution is prepared in a single-dose dosage form. In some embodiments, the aqueous solution is prepared in a multi-dose dosage form. In some embodiments, the aqueous solution is prepared as a ready-to-use formulation.

In some embodiments, the method of preparing AS12 does not include lyophilizing the aqueous solution.

However, in some embodiments, the method of preparation herein can also comprise lyophilizing the aqueous solution herein to form a lyophilized powder, which can be reconstituted prior to use.

It should be noted that the pharmaceutical composition or aqueous solution prepared by any of the methods herein is also a novel composition of the present disclosure. Typically, the pharmaceutical composition or aqueous solution prepared by the methods herein is storage stable, e.g., as described herein.

In some embodiments, the present disclosure also provides a method of stabilizing a liquid pharmaceutical composition comprising bortezomib, more particularly, an aqueous pharmaceutical composition comprising bortezomib. For example, the method can typically include mixing in water (1) bortezomib; (2) a polyhydric alcohol; and (3) an optional water-soluble antioxidant; and optional other ingredients, to form the pharmaceutical composition. In some embodiments, the pharmaceutical composition comprises the optional water-soluble antioxidant, e.g., as described herein. In some embodiments, the pharmaceutical composition comprises one or more optional other ingredients. In some embodiments, the optional other ingredients comprise propylene glycol, benzyl alcohol, a preservative, a chelating agent, an osmotic agent, a buffer, or a combination thereof. In some embodiments, the mixing can comprise: (a) Dissolving the polyhydric alcohol and optional water-soluble antioxidant, and optional other ingredients, in water to form an aqueous excipient mixture; and (b) Adding bortezomib to the aqueous excipient mixture to form the pharmaceutical composition. In some embodiments, the method further comprises sterilizing the pharmaceutical composition. In some embodiments, the method further comprises adjusting the pH of the pharmaceutical composition to about 1.5 to about 5.0, such as about 1.5, about 2, about 3, about 3.5, about 4, about 4.5, about 5, or any ranges between the recited values. In some embodiments, the method further comprises reducing dissolved oxygen in the water and/or pharmaceutical composition. In some embodiments, the method further comprises packaging or sealing the pharmaceutical composition in a container, e.g., an ampoule, a vial, a cartridge, a pre-filled syringe, or an intravenous bag. In some embodiments, the method further comprises reducing oxygen content in the headspace of the container. The ingredients and the respective amount for the pharmaceutical composition can include any of those described herein suitable to provide a storage stable pharmaceutical composition, such as those described for AF1-AF16, as applicable or those shown in [1]-[37], [59], [60], [62], and [69]-[80] in the Brief Summary section herein.

In some more specific embodiments, the present disclosure also provides a method of stabilizing an aqueous solution comprising bortezomib which is suitable for pharmaceutical use (e.g., parenteral injection, such as intravenous or subcutaneous injection). In some embodiments, the method comprises mixing bortezomib with mannitol, sulfobutyl ether beta-cyclodextrin, an optional water-soluble antioxidant, and optional other ingredients, in water to form the aqueous solution. In some embodiments, the aqueous solution comprises the optional water-soluble antioxidant, e.g., as described herein. In some embodiments, the aqueous solution comprises one or more optional other ingredients. In some embodiments, the optional other ingredients comprise propylene glycol, benzyl alcohol, a preservative, a chelating agent, an osmotic agent, a buffer, or a combination thereof. In some embodiments, the mixing can comprise: (a) Dissolving the mannitol, sulfobutyl ether beta-cyclodextrin, optional water-soluble antioxidant, and optional other ingredients in water to form an aqueous excipient mixture; and (b) Adding bortezomib to the aqueous excipient mixture to form the aqueous solution. In some embodiments, the method further comprises sterilizing the aqueous solution. In some embodiments, the method further comprises adjusting the pH of the aqueous solution to about 1.5 to about 5.0, such as about 1.5, about 2, about 3, about 3.5, about 4, about 4.5, about 5, or any ranges between the recited values. In some embodiments, the method further comprises reducing dissolved oxygen in the water, aqueous excipient mixture, and/or aqueous solution. In some embodiments, the method further comprises packaging or sealing the aqueous solution in a container, e.g., an ampoule, a vial, a cartridge, a pre-filled syringe, or an intravenous bag. In some embodiments, the method further comprises reducing oxygen content in the headspace of the container. The ingredients and the respective amount for the aqueous solution can include any of those described herein suitable to provide a storage stable aqueous solution, such as those described for AF12-AF16, as applicable or those shown in [82]-[95] in the Brief Summary section herein.

Methods of Treatment

The pharmaceutical compositions herein have various utilities, such as for inhibiting proteasome function, treating a disease mediated by proteasome, such as for treating cancer, etc.

In some embodiments, the pharmaceutical compositions herein can be used for treating any disease or disorder for which administering bortezomib has been known to be beneficial. Such diseases or disorders include any of those approved by a regulatory agency, such as the U.S. Food and Drug Administration and the alike.

For example, in some embodiments, the present disclosure provides a method of inhibiting proteasome function in a subject in need thereof, the method comprising administering to the subject an effective amount of any of the pharmaceutical compositions herein (e.g., any of those described in [1]-[37], [59], [60], [62] and [95] in the Brief Summary section herein, any of AF1-AF16, etc.).

In some embodiments, the present disclosure provides a method of treating cancer in a subject in need thereof, the method comprising administering to the subject a therapeutically effective amount of any of the pharmaceutical compositions herein (e.g., any of those described in [1]-[37], [59], [60], [62] and [95] in the Brief Summary section herein, any of AF1-AF16, etc.).

In some embodiments, the present disclosure provides a method of treating multiple myeloma in a subject in need thereof, the method comprising administering to the subject a therapeutically effective amount of any of the pharmaceutical compositions herein (e.g., any of those described in [1]-[37], [59], [60], [62] and [95] in the Brief Summary section herein, any of AF1-AF16, etc.).

In some embodiments, the present disclosure provides a method of treating mantle cell lymphoma in a subject in need thereof, the method comprising administering to the subject a therapeutically effective amount of any of the pharmaceutical compositions herein (e.g., any of those described in [1]-[37], [59], [60], [62] and [95] in the Brief Summary section herein, any of AF1-AF16, etc.).

In some embodiments, the present disclosure provides a method of treating a disease or disorder for which bortezomib is indicated for or known to be beneficial, the method comprising administering to a subject in need a therapeutically effective amount of any of the pharmaceutical compositions herein (e.g., any of those described in [1]-[37], [59], [60], [62] and [95] in the Brief Summary section herein, any of AF1-AF16, etc.).

Typically, the method of treatment herein comprises administering the pharmaceutical composition herein intravenously or subcutaneously.

The pharmaceutical compositions herein can be used as a monotherapy or in a combination therapy. When used in a combination therapy, one or more of the pharmaceutical compositions herein can be administered with an additional therapy (e.g., an additional anticancer therapy) either concurrently or sequentially in any order.

The dosing regimen of using the pharmaceutical compositions herein is not particularly limited. For example, in some embodiments, one or more of the pharmaceutical compositions herein can be administered to a subject in need according to a treatment regimen described in the U.S. FDA approved Velcade label, the Prescribing Information for Velcade, revised Apr. 2019, the content of which is incorporated by reference in its entirety. For example, in some embodiments, one or more of the pharmaceutical compositions herein can be administered to a subject in need at a starting dose of about 1.3 mg/m2 either as a 3 to 5 second bolus intravenous injection or subcutaneous injection. In some embodiments, one or more of the pharmaceutical compositions herein can be administered to a subject in need (e.g., subject having previously untreated multiple myeloma) in combination with oral melphalan and oral prednisone. In some embodiments, one or more of the pharmaceutical compositions herein can be administered to a subject in need (e.g., subject having previously untreated Mantle Cell Lymphoma) administered intravenously in combination with intravenous rituximab, cyclophosphamide, doxorubicin and oral prednisone.

Definition

Unless defined otherwise, all technical and scientific terms used herein have the same meaning as commonly understood by one of ordinary skill in the art to which the disclosure pertains.

It is understood that wherever embodiments, are described herein with the language "comprising" otherwise analogous embodiments, described in terms of "containing" "consisting of" and/or "consisting essentially of" are also provided. However, when used in the claims as transitional phrases, each should be interpreted separately and in the appropriate legal and factual context (e.g., in claims, the transitional phrase "comprising" is considered more of an open-ended phrase while "consisting of" is more exclusive and "consisting essentially of" achieves a middle ground).

As used herein, the singular form "a", "an", and "the", includes plural references unless it is expressly stated or is unambiguously clear from the context that such is not intended.

As used herein, the term "about" modifying an amount related to the invention refers to variation in the numerical quantity that can occur, for example, through routine testing and handling; through inadvertent error in such testing and handling; through differences in the manufacture, source, or purity of ingredients employed in the invention; and the like. As used herein, "about" a specific value also includes the specific value, for example, about 10% includes 10%. Whether or not modified by the term "about", the claims include equivalents of the recited quantities. In one embodiment, the term "about" means within 20% of the reported numerical value.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Headings and subheadings are used for convenience and/or formal compliance only, do not limit the subject technology, and are not referred to in connection with the interpretation of the description of the subject technology. Features described under one heading or one subheading of the subject disclosure may be combined, in various embodiments, with features described under other headings or subheadings. Further it is not necessarily the case that all features under a single heading or a single subheading are used together in embodiments.

The term "polyhydroxy containing compounds" means compounds that have two or more hydroxyl groups separated by at least two connecting atoms (i.e. C, N, S or O).

The term "solution" means a homogeneous liquid phase containing two or more Substances, where the two Substances are intimately combined so as to behave physically as a single phase.

As used herein, a pharmaceutical composition that is "free of" of an ingredient should be understood that the pharmaceutical composition does not include the ingredient in a detectable amount. Typically, such pharmaceutical composition can be prepared without using the ingredient. For example, when it is said that a composition is free of a water-soluble cyclodextrin, the composition does not include any detectable amount of water-soluble cyclodextrin. When it is said that a composition is free of a chelating agent described herein, the composition does not include any detectable amount of the chelating agents described herein. Other expressions should be understood similarly.

As used herein, a pharmaceutical composition that is "essentially free of" of an ingredient should be understood that the pharmaceutical composition does not include the ingredient in an amount greater than 5% (w/v). For example, unless otherwise specified, the term "essentially organic solvent free" or "essentially free of an organic solvent" when used in connection with a composition means that the composition does not include more than 5% (w/v) of any organic solvent. Other expressions should be understood similarly.

As used herein, a pharmaceutical composition that is "substantially free of" of an ingredient should be understood that the pharmaceutical composition does not include the ingredient in an amount greater than 15% (w/v), more preferably, the pharmaceutical composition does not include the ingredient in an amount greater than 10% (w/v).

The term "subject" (alternatively referred to herein as "patient") as used herein, refers to an animal, preferably a mammal, most preferably a human, who has been the object of treatment, observation or experiment.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated.

EXAMPLES

For illustration purpose only, the following are selected examples. The ingredients used for the examples are generally commercially available. For example, bortezomib was obtained from LC Laboratories, Cat. No. B-1408. Mannitol Multi-Compendial, was obtained from JI Baker, Cat No. 2553-QM. SBECD: Betadex sulfobutyl ether sodium, USP, was obtained from vendor in Shandong China, HPBCD: Betadex Hydroxylpropyl, USP, was also obtained from vendor in Shandong, China. L-Methionine USP, EP, JP, was obtained from Sigma-Aldrich, Cat, No, 64319. Benzyl alcohol USP/NF, was obtained from EMD Cat. No. 100987. Excipients used for the examples are pharmaceutical grades, or in compliance with USP.

Example 1. Preparation of Bortezomib Formulations and Stability Studies

The following shows a general procedure for preparing the bortezomib formulations, including Formulations I-1, I-2, 1-3, II-1, II-2, II-3, II-4, III-1, III-2, IV-1, IV-2, IV-3, V-1, V-2, V-3, V-4, and V-5.

1. Add a suitable amount of water for injection in a suitable sized container (compounding vessel);
2. Alternatively, Reduce dissolved oxygen in the water by inert gas (such as N2 or Ar) sparging or other approaches suitable for pharmaceutical manufacturing;
3. Add the excipients/stabilizers (such mannitol, SBECD) one by one after each is dissolved;
4. Add any other optional excipients, such as buffer agents, chelating agents, antimicrobial preservatives, etc. one by one and mix until dissolved;
5. Add the antioxidant (such as methionine) and mix until dissolved;

6. Add the drug substance with or without first dissolving in a small amount of solvent (such as propylene glycol, benzyl alcohol, ethanol, etc.) and mix until dissolved; Alternatively, the drug substance can be added after heating Step 5 solution to about 30-40° C., and mix until drug substance dissolved; then cool the solution to room temperature;
7. Adjust solution pH to the target pH using a HCl. and/or NaOH solution;
8. Add sufficient amount of water for injection to the final volume of the intended batch size, and mix solution to homogenous;
9. Filter the final solution through 0.2 μm in sterilizing filter and fill and seal into suitable containers; alternatively, inert gas can be used for replacing the air in the final containers.

The formulations I-1, I-2, I-3, II-1, II-2, II-3, II-4, III-1, III-2, IV-1, IV-2, IV-3, V-1, V-2, V-3, V-4, and V-5 prepared were tested for storage stabilities at different temperatures, 5° C., 25° C. or 40° C. HPLC was used to analyze bortezomib and relevant impurities. Four specific impurities A, D, C1, and C2 as well as any unknown impurities are analyzed in addition to the total amount of impurities. The level of impurities is expressed as % HPLC peak area, unless otherwise specified.

The HPLC conditions used are the following:

| HPLC Column | XBridge C18, 5μ, 4.6 × 250 mm, Part # 186003117 | | | | |
|---|---|---|---|---|---|
| Gradient Profile | Time (mm) | A (%) | B (%) | C (%) | Curve |
| | 0.0 | 71.5 | 28.5 | 0.0 | — |
| | 20.0 | 71.5 | 28.5 | 0.0 | 6 |
| | 30.0 | 65.0 | 35.0 | 0.0 | 6 |
| | 35.1 | 0.0 | 0.0 | 100.0 | 6 |
| | 50.0 | 0.0 | 0.0 | 100.0 | 6 |
| | 50.1 | 71.5 | 28.5 | 0.0 | 6 |
| | 60.0 | 71.5 | 28.5 | 0.0 | 6 |
| Column Temp | 35° C. | | | | |
| Sample Temp. | 5° C. | | | | |
| UV Detector | 270 nm | | | | |
| Flow Rate | 1.0 mL/min | | | | |
| Injection Vol. | 5 μL for standard, 10 μL for samples | | | | |
| Run Time | 50 min | | | | |
| Bortezomib Retention Time | about 11.4 min | | | | |

Mobile phases: A: 0.1% Formic Acid in Water; B: 0.1% Formic Acid in Acetonitrile; and C: 5% Acetonitrile in Water.

The four specific impurities A, D, C1, and C2 are believed to have the structures showing in the following scheme:

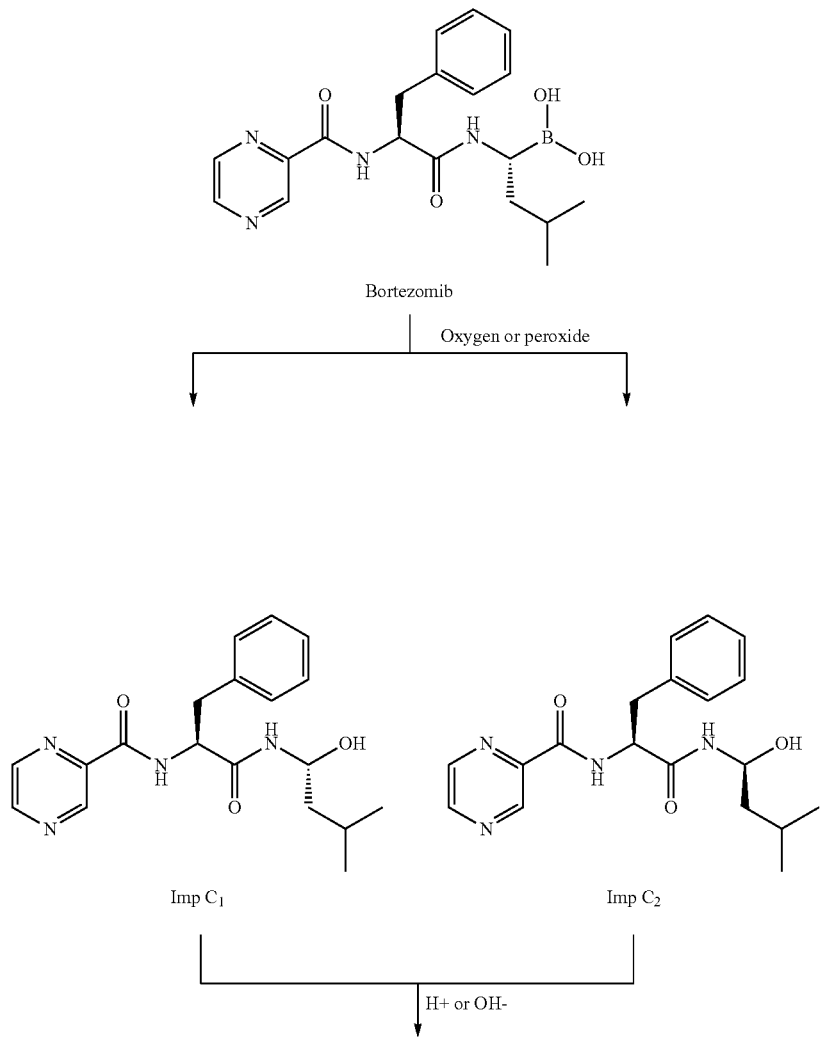

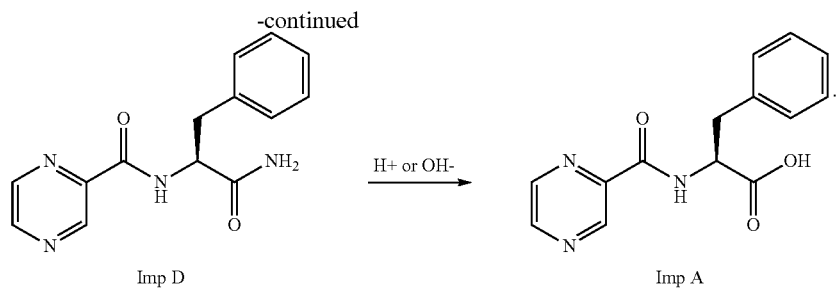

The four specific impurities A, D, C1, and C2 can also be identified by relative retention times as shown in the table below. See also FIG. 1.

Relative Retention Times and Relative Response Factors

| Compound | Retention Time (min) | Relative Retention Time (RRT) | Relative Response Factor (RRF) |
|---|---|---|---|
| Placebo* | 5.4 | 0.48 | NA |
| Impurity D | 5.0 | 0.44 | TBD |
| Impurity A | 7.7 | 0.68 | TBD |
| Bortezomib | 11.4 | 1.00 | 1.00 |
| Impurity C1 | 16.0 | 1.41 | TBD |
| Impurity C2 | 22.2 | 1.96 | TBD |
| Unknown Impurity | NA | NA | 1.00 |

*For indentification purpose only.

Total Impurities=Sum of each individual impurity equal to or greater than 0.10%

Example 2. Preparation of Group I Bortezomib Formulations

Formulations I-1, 1-2, and 1-3 were prepared using the general procedure described in Example 1. Formulation details and results of stability studies are shown in Tables 1A and 1B.

TABLE 1A
Group I Formulations and Stability Data

| | Formulation Ingredients | | I-1 | I-2 | I-3 |
|---|---|---|---|---|---|
| Bortezomib, 1 mg/mL | HP-β-CD | | — | 100 | — |
| | SBE-β-CD | | 100 | — | — |
| | Mannitol | | 100 | 100 | 100 |
| | Propylene glycol | | 40.0 | 40.0 | 40.0 |
| | Methionine | | 2.0 | 2.0 | — |
| | Sodium metabisulfite | | — | — | 2.0 |
| | EDTA | | 0.5 | 0.5 | 0.5 |
| | pH | | 2.0 | 2.0 | 2.0 |
| 40° C. | Initial | | 100% | 100% | 100% |
| | 0.5 | | 99.2% | 98.1% | 98.1% |
| | 1 | | 96.0% | 95.9% | 95.9% |
| | 2 | | 94.0% | 93.6% | 93.6% |
| | 3 | | 88.2% | 90.8% | 90.8% |

*All amounts for the ingredients of the formulation have a unit of mg/mL.

TABLE 1B
Impurity Analysis of Group I Formulations

| Formulation | | Impurities (% peak area) at 40° C. | | | | |
|---|---|---|---|---|---|---|
| | | D | A | C1 | C2 | Total Imp |
| I-1 | Initial | 0.080 | 0.040 | 0.030 | 0.120 | 0.460 |
| | 0.5 | 0.300 | 1.330 | ND | ND | 1.790 |
| | 1 | 1.130 | 2.820 | ND | ND | 4.110 |
| | 2 | 1.170 | 5.760 | ND | ND | 7.280 |
| | 3 | 1.310 | 8.340 | ND | ND | 10.120 |
| I-2 | Initial | 0.080 | 0.030 | 0.060 | 0.140 | 0.420 |
| | 0.5 | 0.290 | 0.690 | 0.040 | 0.100 | 1.210 |
| | 1 | 1.240 | 1.720 | 0.090 | 0.220 | 3.470 |
| | 2 | 2.620 | 3.410 | 0.120 | 0.310 | 6.640 |
| | 3 | 3.840 | 5.270 | 0.130 | 0.290 | 9.720 |
| I-3 | Initial | 0.090 | 0.030 | 0.040 | 0.080 | 0.400 |
| | 0.5 | 0.310 | 0.850 | ND | ND | 1.270 |
| | 1 | 0.300 | 1.400 | ND | ND | 2.330 |
| | 2 | 0.580 | 3.140 | ND | ND | 4.200 |
| | 3 | 0.760 | 4.400 | 0.030 | 0.070 | 5.870 |

Example 3. Preparation of Group II Bortezomib Formulations

Formulations II-1, 11-2, 11-3, and 11-4 were prepared using the general procedure described in Example 1. Formulation details and results of stability studies are shown in Tables 2A-2D.

TABLE 2A
Group II Formulations and Stability Data

| | | Formulation* | | | |
|---|---|---|---|---|---|
| Ingredients | | II-1 | II-2 | II-3 | II-4 |
| Bortezomib, 1 mg/mL | Mannitol | 100 | 100 | 100 | 100 |
| | Propylene glycol | 40 | 40 | 40 | 40 |
| | Benzyl alcohol | 16.7 | 16.7 | 16.7 | 16.7 |
| | Methionine | 2.0 | 2.0 | 2.0 | 2.0 |
| | EDTA | 0.5 | 0.5 | 0.5 | 0.5 |
| | Glycine buffer to pH | 2.0 | 2.5 | 3.0 | 3.5 |
| 5° C. | Initial | 100.0% | 100.0% | 100.0% | 100.0% |
| | 1 | 100.8% | 99.9% | 101.5% | 100.7% |
| | 3 | 98.9% | 99.2% | 98.6% | 99.5% |
| 25° C. | 0.5 | 99.4% | 98.8% | 97.4% | 98.6% |
| | 1 | 100.2% | 98.9% | 100.8% | 99.9% |
| | 2 | 98.7% | 97.8% | 100.4% | 97.3% |
| | 3 | 96.8% | 95.9% | 98.4% | 99.5% |
| 40° C. | 0.5 | 99.5% | 97.1% | 98.0% | 97.6% |
| | 1 | 97.5% | 96.7% | 98.0% | 97.2% |
| | 2 | 93.0% | 95.2% | 92.9% | 95.8% |
| | 3 | 89.3% | 83.9% | 91.9% | 92.0% |

*All amounts for the ingredients of the formulation have a unit of mg/mL.

TABLE 2B

Impurity Analysis of Group II Formulations at 5° C.

| Formulation | Time (month) | D | A | RRT0.87 | C1 | C2 | Total Imp |
|---|---|---|---|---|---|---|---|
| II-1 | Initial | 0.07 | 0.02 | 0.72 | 0.09 | 0.21 | 1.37 |
|  | 1 | 0.12 | 0.07 | 0.44 | 0.00 | 0.06 | 0.98 |
|  | 3 | 0.23 | 0.15 | 0.39 | 0.03 | 0.12 | 1.29 |
| II-2 | Initial | 0.07 | 0.02 | 0.57 | 0.15 | 0.29 | 1.36 |
|  | 1 | 0.09 | 0.07 | 0.41 | 0.07 | 0.21 | 1.19 |
|  | 3 | 0.16 | 0.17 | 0.37 | 0.10 | 0.25 | 1.38 |
| II-3 | Initial | 0.07 | 0.02 | 0.51 | 0.30 | 0.39 | 1.48 |
|  | 1 | 0.08 | 0.08 | 0.43 | 0.17 | 0.34 | 1.34 |
|  | 3 | 0.10 | 0.16 | 0.34 | 0.18 | 0.38 | 1.47 |
| II-4 | Initial | 0.07 | 0.02 | 0.48 | 0.61 | 0.31 | 1.64 |
|  | 1 | 0.07 | 0.07 | 0.45 | 0.25 | 0.49 | 1.52 |
|  | 3 | 0.09 | 0.17 | 0.36 | 0.28 | 0.55 | 1.79 |

TABLE 2C

Impurity Analysis of Group II Formulations at 25° C.

| Formulation | Time (month) | D | A | RRT0.87 | C1 | C2 | Total Imp |
|---|---|---|---|---|---|---|---|
| II-1 | 0.5 | 0.33 | 0.20 | 0.49 | 0.00 | 0.06 | 1.33 |
|  | 1 | 0.66 | 0.42 | 0.52 | 0.03 | 0.07 | 1.91 |
|  | 2 | 1.18 | 0.77 | 0.61 | 0.00 | 0.09 | 2.88 |
|  | 3 | 1.44 | 1.20 | 0.64 | 0.04 | 0.10 | 3.67 |
| II-2 | 0.5 | 0.18 | 0.19 | 0.38 | 0.06 | 0.14 | 1.21 |
|  | 1 | 0.36 | 0.43 | 0.42 | 0.09 | 0.22 | 1.75 |
|  | 2 | 0.71 | 0.71 | 0.49 | 0.10 | 0.21 | 2.46 |
|  | 3 | 1.02 | 1.05 | 0.50 | 0.16 | 0.30 | 3.34 |
| II-3 | 0.5 | 0.12 | 0.18 | 0.38 | 0.17 | 0.32 | 1.34 |
|  | 1 | 0.20 | 0.38 | 0.41 | 0.21 | 0.38 | 1.75 |
|  | 2 | 0.33 | 0.68 | 0.38 | 0.21 | 0.41 | 2.18 |
|  | 3 | 0.49 | 1.01 | 0.38 | 0.25 | 0.48 | 2.95 |
| II-4 | 0.5 | 0.10 | 0.19 | 0.39 | 0.29 | 0.49 | 1.69 |
|  | 1 | 0.14 | 0.38 | 0.39 | 0.29 | 0.53 | 1.87 |
|  | 2 | 0.20 | 0.68 | 0.40 | 0.30 | 0.57 | 2.31 |
|  | 3 | 0.27 | 1.00 | 0.34 | 0.37 | 0.69 | 3.10 |

TABLE 2D

Impurity Analysis of Group II Formulations at 40° C.

| Formulation | Time (month) | D | A | RRT0.87 | C1 | C2 | Total Imp |
|---|---|---|---|---|---|---|---|
| II-1 | 0.5 | 0.62 | 0.83 | 0.45 | 0.00 | 0.00 | 2.06 |
|  | 1 | 1.14 | 2.13 | 0.64 | 0.00 | 0.00 | 4.04 |
|  | 2 | 1.92 | 4.38 | 0.82 | 0.00 | 0.00 | 7.25 |
|  | 3 | 2.33 | 6.74 | 0.93 | 0.00 | 0.02 | 10.36 |
| II-2 | 0.5 | 0.52 | 0.77 | 0.36 | 0.00 | 0.06 | 1.94 |
|  | 1 | 0.90 | 1.91 | 0.44 | 0.05 | 0.07 | 3.50 |
|  | 2 | 1.31 | 3.71 | 0.46 | 0.00 | 0.04 | 5.63 |
|  | 3 | 1.75 | 5.52 | 0.47 | 0.00 | 0.00 | 8.04 |
| II-3 | 0.5 | 0.32 | 0.75 | 0.33 | 0.10 | 0.21 | 1.97 |
|  | 1 | 0.65 | 1.86 | 0.38 | 0.15 | 0.24 | 3.40 |
|  | 2 | 1.18 | 3.48 | 0.35 | 0.09 | 0.17 | 5.41 |
|  | 3 | 1.53 | 5.29 | 0.30 | 0.05 | 0.16 | 7.60 |
| II-4 | 0.5 | 0.24 | 0.75 | 0.32 | 0.26 | 0.47 | 2.29 |
|  | 1 | 0.44 | 1.83 | 0.37 | 0.27 | 0.52 | 3.56 |
|  | 2 | 0.87 | 3.46 | 0.29 | 0.26 | 0.47 | 5.55 |
|  | 3 | 1.29 | 5.09 | 0.23 | 0.22 | 0.42 | 7.65 |

Example 4. Preparation of Group III Bortezomib Formulations

Formulations III-1 and III-2 were prepared using the general procedure described in Example 1. Formulation details and results of stability studies are shown in Tables 3A-3D.

TABLE 3A

Group III Formulations and Stability Data

| Formulation Ingredients | | III-1 | III-2 |
|---|---|---|---|
| Bortezomib, 2.5 mg/mL | Mannitol | 100 | 100 |
|  | SBE-β-CD | 100 | 100 |
|  | Propylene glycol | — | 40 |
|  | Benzyl alcohol | 16.7 | — |
|  | Methionine | 2.0 | 2.0 |
|  | EDTA | 0.5 | 0.5 |
|  | pH | 3.0 | 3.0 |
| 5° C. | Initial | 100.0% | 100.0% |
|  | 1 | 99.5% | 99.5% |
|  | 3 | 98.6% | 98.6% |
| 25° C. | 1 | 99.5% | 99.6% |
|  | 2 | 99.9% | 100.1% |
|  | 3 | 96.6% | 97.3% |
| 40° C. | 1 | 99.2% | 100.1% |
|  | 2 | 95.6% | 95.8% |
|  | 3 | 91.3% | 92.0% |

TABLE 3B

Impurity Analysis of Group III Formulations at 5° C.

| Formulation | Time (month) | D | A | RRT0.88 | C1 | C2 | Total Imp |
|---|---|---|---|---|---|---|---|
| III-1 | Initial | 0.06 | 0.02 | 0.03 | 0.10 | 0.25 | 0.57 |
|  | 1 | 0.08 | 0.07 | 0.03 | 0.07 | 0.14 | 0.42 |
|  | 3 | 0.10 | 0.13 | 0.03 | 0.06 | 0.16 | 0.50 |
| III-2 | Initial | 0.09 | 0.03 | ND | 0.09 | 0.23 | 0.57 |
|  | 1 | 0.10 | 0.06 | ND | 0.07 | 0.19 | 0.46 |
|  | 3 | 0.13 | 0.12 | ND | 0.04 | 0.15 | 0.48 |

TABLE 3C

Impurity Analysis of Group III Formulations at 25° C.

| Formulation | Time (month) | D | A | RRT0.88 | C1 | C2 | Total Imp |
|---|---|---|---|---|---|---|---|
| III-1 | 1 | 0.20 | 0.33 | 0.02 | 0.06 | 0.12 | 0.76 |
|  | 2 | 0.30 | 0.62 | 0.04 | 0.06 | 0.13 | 1.19 |
|  | 3 | 0.47 | 0.89 | 0.09 | 0.07 | 0.21 | 1.73 |
| III-2 | 1 | 0.65 | 1.61 | 0.08 | 0.04 | 0.12 | 2.56 |
|  | 2 | 0.91 | 3.12 | 0.10 | 0.04 | 0.12 | 4.35 |
|  | 3 | 1.31 | 4.38 | 0.11 | 0.03 | 0.12 | 6.02 |

TABLE 3D

Impurity Analysis of Group III Formulations at 40° C.

| Formulation | Time (month) | D | A | RRT0.88 | C1 | C2 | Total Imp |
|---|---|---|---|---|---|---|---|
| III-1 | 1 | 0.26 | 0.32 | ND | 0.04 | 0.09 | 0.74 |
|  | 2 | 0.38 | 0.61 | ND | 0.05 | 0.12 | 1.19 |
|  | 3 | 0.46 | 0.86 | ND | 0.04 | 0.10 | 1.46 |
| III-2 | 1 | 0.64 | 1.51 | ND | 0.03 | 0.07 | 2.32 |
|  | 2 | 1.06 | 2.99 | ND | 0.06 | 0.10 | 4.31 |
|  | 3 | 1.71 | 4.36 | ND | 0.05 | 0.14 | 6.36 |

Example 5. Preparation of Group IV Bortezomib Formulations

Formulations IV-1, IV-2, and IV-3 were prepared using the general procedure described in Example 1. Formulation details and results of stability studies are shown in Tables 4A-4D.

TABLE 4A

Group IV Formulations and Stability Data

|  |  | Formulation* | | |
|---|---|---|---|---|
| Ingredients | | IV-1 | IV-2 | IV-3 |
| Bortezomib, 1 mg/mL | SBECD | 100 | 100 | 100 |
|  | Mannitol | 100 | 100 | 100 |
|  | Benzyl alcohol | 16.7 | 16.7 | — |
|  | Methionine | 2.0 | 2.0 | 2.0 |
|  | EDTA | 0.5 | — | — |
|  | Glycine buffer to pH | 3.5 | 3.5 | 3.5 |
| 5° C. | Initial | 100.0% | 100.0% | 100.0% |
|  | 1 | 99.7% | 100.6% | 98.7% |
|  | 3 | 102.4% | 99.1% | 99.7% |
| 25° C. | 0.5 | 97.8% | 99.8% | 98.9% |
|  | 1 | 99.8% | 100.5% | 98.3% |
|  | 2 | 98.6% | 97.4% | 95.9% |
|  | 3 | 100.3% | 97.2% | 96.8% |
| 40° C. | 0.5 | 99.6% | 99.3% | 98.1% |
|  | 1 | 98.9% | 99.0% | 97.1% |
|  | 2 | 96.0% | 92.7% | 90.6% |
|  | 3 | 92.9% | 91.1% | 89.0% |

*All amounts for the ingredients of the formulation have a unit of mg/mL.

TABLE 4B

Impurity Analysis of Group IV Formulations at 5° C.

| Formulation | Time (month) | D | A | C1 | C2 | Total Imp |
|---|---|---|---|---|---|---|
| IV-1 | Initial | 0.08 | 0.02 | 0.25 | 0.36 | 0.90 |
|  | 1 | 0.08 | 0.07 | 0.10 | 0.30 | 0.73 |
|  | 3 | 0.10 | 0.12 | 0.12 | 0.28 | 0.70 |
| IV-2 | Initial | 0.07 | 0.03 | 0.25 | 0.33 | 0.88 |
|  | 1 | 0.09 | 0.07 | 0.10 | 0.34 | 0.84 |
|  | 3 | 0.10 | 0.13 | 0.12 | 0.31 | 0.81 |
| IV-3 | Initial | 0.09 | 0.03 | 0.21 | 0.22 | 0.69 |
|  | 1 | 0.11 | 0.07 | 0.08 | 0.28 | 0.68 |
|  | 3 | 0.13 | 0.14 | 0.08 | 0.20 | 0.72 |

TABLE 4C

Impurity Analysis of Group IV Formulations at 25° C.

| Formulation | Time (month) | D | A | C1 | C2 | Total Imp |
|---|---|---|---|---|---|---|
| IV-1 | 0.5 | 0.11 | 0.16 | 0.10 | 0.30 | 0.78 |
|  | 1 | 0.15 | 0.32 | 0.12 | 0.31 | 0.97 |
|  | 2 | 0.22 | 0.61 | 0.14 | 0.35 | 1.43 |
|  | 3 | 0.26 | 0.88 | 0.13 | 0.23 | 1.60 |
| IV-2 | 0.5 | 0.12 | 0.16 | 0.12 | 0.33 | 0.86 |
|  | 1 | 0.17 | 0.32 | 0.16 | 0.41 | 1.30 |
|  | 2 | 0.30 | 0.68 | 0.23 | 0.59 | 2.05 |
|  | 3 | 0.39 | 0.91 | 0.22 | 0.50 | 2.25 |
| IV-3 | 0.5 | 0.15 | 0.17 | 0.10 | 0.29 | 0.85 |
|  | 1 | 0.24 | 0.37 | 0.14 | 0.34 | 1.29 |
|  | 2 | 0.46 | 0.79 | 0.15 | 0.42 | 2.07 |
|  | 3 | 0.62 | 1.09 | 0.19 | 0.43 | 2.55 |

TABLE 4D

Impurity Analysis of Group IV Formulations at 40° C.

| Formulation | Time (month) | D | A | C1 | C2 | Total Imp |
|---|---|---|---|---|---|---|
| IV-1 | 0.5 | 0.26 | 0.74 | 0.12 | 0.27 | 1.51 |
|  | 1 | 0.43 | 1.54 | 0.11 | 0.23 | 2.47 |
|  | 2 | 0.77 | 3.39 | 0.08 | 0.23 | 4.72 |
|  | 3 | 1.19 | 4.79 | 0.11 | 0.21 | 6.64 |
| IV-2 | 0.5 | 0.32 | 0.72 | 0.17 | 0.40 | 1.76 |
|  | 1 | 0.55 | 1.56 | 0.16 | 0.38 | 3.07 |
|  | 2 | 1.63 | 3.49 | 0.21 | 0.55 | 6.40 |
|  | 3 | 2.46 | 5.01 | 0.25 | 0.52 | 9.16 |
| IV-3 | 0.5 | 0.38 | 0.73 | 0.12 | 0.30 | 1.63 |
|  | 1 | 0.93 | 1.71 | 0.13 | 0.34 | 3.29 |
|  | 2 | 2.31 | 3.85 | 0.16 | 0.48 | 7.12 |
|  | 3 | 3.37 | 5.57 | 0.16 | 0.41 | 10.1 |

Example 6. Preparation of Group V Bortezomib Formulations

Formulations V-1, V-2, V-3, V-4, and V-5 were prepared using the general procedure described in Example 1. Formulation details and results of stability studies are shown in Tables 5A-5C.

TABLE 5A

Group V Formulations and Stability Data

|  |  | Formulation* | | | | |
|---|---|---|---|---|---|---|
| Ingredients | | V-1 | V-2 | V-3 | V-4 | V-5 |
| Bortezomib, 1 mg/mL | Mannitol | 10 | 20 | 40 | 60 | 100 |
|  | Benzyl alcohol | 16.7 | 16.7 | 16.7 | 16.7 | 16.7 |
|  | Methionine | 2.0 | 2.0 | 2.0 | 2.0 | 2.0 |
|  | EDTA | 0.5 | 0.5 | 0.5 | 0.5 | 0.5 |
|  | pH | 3.5 | 3.5 | 3.5 | 3.5 | 3.5 |
| 25° C. | Initial | 100.0% | 100.0% | 100.0% | 100.0% | 100.0% |
|  | 0.5 | 98.0% | 96.6% | 97.3% | 97.9% | 101.1% |
|  | 1 | 96.7% | 96.5% | 97.8% | 98.5% | 100.5% |
|  | 2 | 95.7% | 94.9% | 95.9% | 96.3% | 100.4% |
|  | 3 | 94.6% | 94.8% | 97.0% | 98.1% | 99.0% |
| 40° C. | 0.5 | 95.9% | 94.1% | 95.8% | 96.2% | 99.8% |
|  | 1 | 92.4% | 92.1% | 93.4% | 94.5% | 98.8% |
|  | 2 | 87.6% | 90.2% | 92.0% | 92.0% | 96.0% |
|  | 3 | 82.8% | 86.4% | 91.6% | 91.7% | 92.2% |

*All amounts for the ingredients of the formulation have a unit of mg/mL.

TABLE 5B

Impurity Analysis of Group V Formulations at 25° C.

| Formulation ID | Time (month) | Impurities (% peak area) at 25° C. | | | | |
|---|---|---|---|---|---|---|
| | | D | A | RRT0.87 | C1 | C2 | Total Imp |
| V-1 | Initial | 0.06 | 0.02 | 0.08 | 0.25 | 0.24 | 0.75 |
| | 0.5 | 0.10 | 0.28 | 0.15 | 0.32 | 0.57 | 1.59 |
| | 1 | 0.19 | 0.50 | 0.30 | 0.74 | 1.27 | 3.13 |
| | 2 | 0.30 | 0.86 | 0.28 | 0.64 | 1.12 | 3.35 |
| | 3 | 0.54 | 1.26 | 0.51 | 1.29 | 2.19 | 5.99 |
| V-2 | Initial | 0.07 | 0.03 | 0.06 | 0.26 | 0.24 | 0.78 |
| | 0.5 | 0.10 | 0.27 | 0.12 | 0.29 | 0.56 | 1.56 |
| | 1 | 0.15 | 0.48 | 0.23 | 0.52 | 0.92 | 2.36 |
| | 2 | 0.26 | 0.83 | 0.23 | 0.54 | 0.96 | 2.93 |
| | 3 | 0.45 | 1.21 | 0.35 | 0.80 | 1.36 | 4.31 |
| V-3 | Initial | 0.07 | 0.03 | 0.06 | 0.23 | 0.21 | 0.72 |
| | 0.5 | 0.09 | 0.26 | 0.07 | 0.21 | 0.41 | 1.19 |
| | 1 | 0.14 | 0.48 | 0.13 | 0.30 | 0.52 | 1.58 |
| | 2 | 0.20 | 0.80 | 0.13 | 0.31 | 0.56 | 2.16 |
| | 3 | 0.24 | 1.17 | 0.16 | 0.44 | 0.73 | 2.77 |
| V-4 | Initial | 0.20 | 0.03 | 0.07 | 0.27 | 0.20 | 0.89 |
| | 0.5 | 0.24 | 0.26 | 0.07 | 0.20 | 0.34 | 1.27 |
| | 1 | 0.26 | 0.46 | 0.09 | 0.21 | 0.36 | 1.38 |
| | 2 | 0.32 | 0.81 | 0.11 | 0.24 | 0.40 | 1.93 |
| | 3 | 0.36 | 1.16 | 0.12 | 0.26 | 0.49 | 2.43 |
| V-5 | Initial | 0.07 | 0.03 | 0.38 | 1.25 | 0.56 | 2.46 |
| | 0.5 | 0.12 | 0.21 | 0.28 | 0.44 | 0.85 | 2.03 |
| | 1 | 0.24 | 0.43 | 0.36 | 0.53 | 1.03 | 2.83 |
| | 2 | 0.29 | 0.70 | 0.27 | 0.52 | 1.01 | 2.98 |
| | 3 | 0.41 | 1.08 | 0.31 | 0.55 | 0.97 | 3.78 |

TABLE 5C

Impurity Analysis of Group V Formulations at 40° C.

| Formulation ID | Time (month) | Impurities (% peak area) at 40° C. | | | | | |
|---|---|---|---|---|---|---|---|
| | | D | A | RRT0.87 | C1 | C2 | Total Imp |
| V-1 | Initial | 0.06 | 0.02 | 0.08 | 0.25 | 0.24 | 0.75 |
| | 0.5 | 0.24 | 1.22 | 0.12 | 0.27 | 0.48 | 2.59 |
| | 1 | 0.91 | 2.32 | 0.36 | 0.74 | 1.25 | 5.66 |
| | 2 | 1.96 | 3.92 | 0.53 | 1.10 | 1.87 | 9.62 |
| | 3 | 4.47 | 5.88 | 0.97 | 1.78 | 3.05 | 16.48 |
| V-2 | Initial | 0.07 | 0.03 | 0.06 | 0.26 | 0.24 | 0.78 |
| | 0.5 | 0.24 | 1.23 | 0.08 | 0.18 | 0.35 | 2.30 |
| | 1 | 0.74 | 2.29 | 0.27 | 0.56 | 0.94 | 4.88 |
| | 2 | 1.00 | 3.83 | 0.22 | 0.45 | 0.80 | 6.37 |
| | 3 | 2.79 | 5.80 | 0.52 | 1.00 | 1.69 | 12.04 |
| V-3 | Initial | 0.07 | 0.03 | 0.06 | 0.23 | 0.21 | 0.72 |
| | 0.5 | 0.22 | 1.18 | 0.06 | 0.17 | 0.31 | 2.14 |
| | 1 | 0.47 | 2.21 | 0.17 | 0.33 | 0.54 | 3.78 |
| | 2 | 0.73 | 3.77 | 0.13 | 0.28 | 0.49 | 5.49 |
| | 3 | 0.94 | 5.62 | 0.14 | 0.27 | 0.47 | 7.59 |
| V-4 | Initial | 0.20 | 0.03 | 0.07 | 0.27 | 0.20 | 0.89 |
| | 0.5 | 0.36 | 1.19 | 0.11 | 0.21 | 0.42 | 2.47 |
| | 1 | 0.54 | 2.12 | 0.15 | 0.29 | 0.48 | 3.66 |
| | 2 | 0.82 | 3.67 | 0.13 | 0.29 | 0.47 | 5.51 |
| | 3 | 1.26 | 5.50 | 0.15 | 0.34 | 0.57 | 7.98 |
| V-5 | Initial | 0.07 | 0.03 | 0.38 | 1.25 | 0.56 | 2.46 |
| | 0.5 | 0.33 | 0.83 | 0.29 | 0.41 | 0.78 | 2.79 |
| | 1 | 0.85 | 2.05 | 0.34 | 0.50 | 0.88 | 4.79 |
| | 2 | 1.22 | 3.48 | 0.22 | 0.42 | 0.75 | 6.30 |
| | 3 | 1.93 | 5.65 | 0.26 | 0.39 | 0.68 | 9.44 |

The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A pharmaceutical composition comprising (1) bortezomib; (2) mannitol; (3) a water-soluble antioxidant; (4) a buffer; and (5) a chelating agent, wherein the pharmaceutical composition is a ready-to-use aqueous solution, wherein the mannitol is in an amount of about 50 mg/ml to about 150 mg/ml,
the aqueous solution comprises water in an amount of greater than 50% by weight,
the bortezomib is present in the pharmaceutical composition in a concentration ranging from about 0.5 mg/mL to about 3.5 mg/ml;
the water-soluble antioxidant is present in a concentration of about 1 mg/mL to about 5 mg/ml;
the chelating agent is present in a concentration of about 0.1 mg/mL to about 1 mg/ml;
the pharmaceutical composition has a pH of about 3.0 to about 5.0, and
wherein when stored at 40° C. for 3 months, the pharmaceutical composition is characterized in that the impurity with a relative retention time to bortezomib of about 0.87-0.88 is in an amount of 0.5% or less.

2. The pharmaceutical composition of claim 1, wherein the weight ratio of bortezomib to mannitol ranges from about 1:20 to about 1:200.

3. The pharmaceutical composition of claim 1, wherein the pharmaceutical composition further comprises a water-soluble cyclodextrin.

4. The pharmaceutical composition of claim 1, wherein pharmaceutical composition further comprises propylene glycol, benzyl alcohol, or a combination thereof.

5. The pharmaceutical composition of claim 4, wherein the propylene glycol, benzyl alcohol, or combination thereof is present in a concentration of about 5 mg/mL to about 100 mg/mL.

6. The pharmaceutical composition of claim 1, wherein the water-soluble antioxidant comprises a sulfur containing amino acid, or the water-soluble antioxidant comprises monothioglycerol, sodium metabisulfite, butylated hydroxyanisole and/or butylated hydroxytoluene.

7. The pharmaceutical composition of claim 1, further comprising a preservative, an osmotic agent, or a combination thereof.

8. The pharmaceutical composition of claim 1, which is in a single-dose or a multi-dose dosage form, packaged in an ampoule, a vial, a cartridge, a pre-filled syringe, or an intravenous bag.

9. A pharmaceutical composition comprising (1) bortezomib; (2) mannitol; (3) methionine; (4) EDTA and (5) glycine, wherein the pharmaceutical composition comprises water in an amount of greater than 50% by weight,
the bortezomib is present in the pharmaceutical composition in a concentration ranging from about 0.5 mg/mL to about 3.5 mg/mL,
the mannitol is present in the pharmaceutical composition in a concentration ranging from about 50 mg/mL to about 150 mg/mL,
the weight ratio of bortezomib to mannitol in the pharmaceutical composition ranges from about 1:20 to about 1:200,
methionine is present in the pharmaceutical composition in a concentration of about 1 mg/mL to about 5 mg/mL,
EDTA is present in the pharmaceutical composition in a concentration of about 0.1 mg/mL to about 1 mg/mL, and
the pharmaceutical composition has a pH of about 3.0 to about 5.0, and
wherein when stored at 40°C for 3 months, the pharmaceutical composition is characterized in that the impurity with a relative retention time to bortezomib of about 0.87-0.88 is in an amount of 0.5% or less.

10. A method of producing the pharmaceutical composition of claim 1, the method comprising mixing in water (1) bortezomib with (2) mannitol; (3) the water-soluble antioxidant, (4) the buffer; and (5) the chelating agent, and optional other ingredients, to form the pharmaceutical composition.

11. A method of inhibiting proteasome function in a subject in need thereof, the method comprising administering to the subject an effective amount of the pharmaceutical composition of claim 1.

12. A method of treating multiple myeloma and/or mantle cell lymphoma in a subject in need thereof, the method comprising administering to the subject a therapeutically effective amount of the pharmaceutical composition of claim 1.

13. The pharmaceutical composition of claim 1, wherein the water-soluble antioxidant is methionine.

14. The pharmaceutical composition of claim 1, wherein the chelating agent is EDTA.

15. The pharmaceutical composition of claim 1, wherein the buffer is glycine.

16. The pharmaceutical composition of claim 1, wherein the pharmaceutical composition has a pH of about 3 to about 4.5.

* * * * *